United States Patent
Beasley et al.

(10) Patent No.: US 8,608,713 B2
(45) Date of Patent: *Dec. 17, 2013

(54) SEPTUM FEATURE FOR IDENTIFICATION OF AN ACCESS PORT

(75) Inventors: Jim C. Beasley, Phoenix, AZ (US); Eddie K. Burnside, Bountiful, UT (US); Jay Gerondale, Newbury Park, CA (US); Steven Tallarida, Mansfield, MA (US); Kelly B. Powers, North Salt Lake, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/471,219

(22) Filed: May 14, 2012

(65) Prior Publication Data
US 2012/0226244 A1 Sep. 6, 2012

Related U.S. Application Data

(63) Continuation of application No. 11/320,223, filed on Dec. 28, 2005, now Pat. No. 8,177,762, which is a continuation-in-part of application No. 10/374,000, filed on Feb. 25, 2003, now Pat. No. 7,713,251, which is a continuation of application No. 09/582,406, filed as application No. PCT/US99/28695 on Dec. 3, 1999, now Pat. No. 6,527,754.

(60) Provisional application No. 60/111,257, filed on Dec. 7, 1998, provisional application No. 60/658,518, filed on Mar. 4, 2005.

(51) Int. Cl.
*A61M 37/00* (2006.01)

(52) U.S. Cl.
USPC .................................................. 604/288.02

(58) Field of Classification Search
USPC ........................................ 604/288.01, 288.02
See application file for complete search history.

(56) References Cited

U.S. PATENT DOCUMENTS

| | | | |
|---|---|---|---|
| 445,896 A | 2/1891 | Kinsman |
| 546,440 A | 9/1895 | Tufts |
| 574,387 A | 1/1897 | Buckler |
| 611,357 A | 9/1898 | Dembinski |
| 966,696 A | 8/1910 | Merrill |
| D44,302 S | 7/1913 | Director |
| 1,713,267 A | 5/1929 | Crowley |

(Continued)

FOREIGN PATENT DOCUMENTS

| AU | 2008299945 A1 | 3/2009 |
|---|---|---|
| CA | 2663853 A1 | 4/2008 |

(Continued)

OTHER PUBLICATIONS

PCT/US2008/070330 filed Jul. 17, 2008 Search Report dated Dec. 1, 2008.

(Continued)

*Primary Examiner* — Aarti B Berdichevsky
(74) *Attorney, Agent, or Firm* — Rutan & Tucker, LLP

(57) ABSTRACT

An access port for providing subcutaneous access to a patient, and a method of identifying a subcutaneously implanted access port. The access port includes a body capturing a septum that covers a cavity defined by the body, and a pattern of protrusions extending from an outer surface of the septum away from the cavity, the pattern of protrusions detectable through palpation to identify the access port as a power-injectable port.

19 Claims, 21 Drawing Sheets

(56) References Cited

U.S. PATENT DOCUMENTS

| | | |
|---|---|---|
| 2,029,553 A | 2/1936 | Bartischi et al. |
| D130,852 S | 12/1941 | Rothschild |
| 2,433,480 A | 12/1947 | Rendich |
| 2,891,689 A | 6/1959 | Gould |
| D198,453 S | 6/1964 | Weichselbaum |
| 3,159,175 A | 12/1964 | Macmillan |
| 3,211,431 A | 10/1965 | Meysembourg et al. |
| 3,293,663 A | 12/1966 | Cronin |
| 3,341,417 A | 9/1967 | Sinaiko |
| 3,477,438 A | 11/1969 | Allen et al. |
| 3,518,428 A | 6/1970 | Ring |
| 3,525,357 A | 8/1970 | Koreski |
| 3,529,633 A | 9/1970 | Vailancourt |
| 3,541,438 A | 11/1970 | Nelsen et al. |
| 3,643,358 A | 2/1972 | Morderosian |
| D223,340 S | 4/1972 | Diedrich |
| 3,669,323 A | 6/1972 | Harker et al. |
| 3,674,183 A | 7/1972 | Venable et al. |
| 3,811,466 A | 5/1974 | Ohringer |
| 3,829,904 A | 8/1974 | Ling et al. |
| 3,831,583 A | 8/1974 | Edmunds, Jr. et al. |
| 3,840,009 A | 10/1974 | Michaels et al. |
| 3,853,127 A | 12/1974 | Spademan |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 3,955,594 A | 5/1976 | Snow |
| 3,971,376 A | 7/1976 | Wichterle |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,143,853 A | 3/1979 | Abramson |
| 4,168,586 A | 9/1979 | Samis |
| 4,190,040 A | 2/1980 | Schulte |
| 4,190,057 A | 2/1980 | Hill et al. |
| 4,194,122 A | 3/1980 | Mitchell et al. |
| 4,196,731 A | 4/1980 | Laurin et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| D263,335 S | 3/1982 | Bujan |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,447,237 A | 5/1984 | Frisch et al. |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,479,798 A | 10/1984 | Parks |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,043 A | 12/1985 | Whitehouse et al. |
| 4,559,046 A | 12/1985 | Groshong et al. |
| 4,560,375 A | 12/1985 | Schulte et al. |
| 4,569,675 A | 2/1986 | Prosl et al. |
| 4,571,749 A | 2/1986 | Fischell |
| 4,576,595 A | 3/1986 | Aas et al. |
| 4,610,665 A | 9/1986 | Matsumoto et al. |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,681,560 A | 7/1987 | Schulte et al. |
| 4,684,365 A | 8/1987 | Reinicke |
| 4,685,447 A | 8/1987 | Iversen et al. |
| 4,685,905 A | 8/1987 | Jeanneret nee Aab |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stober et al. |
| 4,707,389 A | 11/1987 | Ward |
| 4,710,167 A | 12/1987 | Lazorthes |
| 4,710,174 A | 12/1987 | Moden et al. |
| 4,718,894 A | 1/1988 | Lazorthes |
| 4,723,947 A | 2/1988 | Konopka |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,784,646 A | 11/1988 | Feingold |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |
| 4,904,241 A | 2/1990 | Bark |
| 4,905,709 A | 3/1990 | Bieganski et al. |
| 4,908,029 A | 3/1990 | Bark et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,961,267 A | 10/1990 | Herzog |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,006,115 A | 4/1991 | McDonald |
| 5,009,391 A | 4/1991 | Steigerwald |
| 5,009,644 A | 4/1991 | McDonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,053,013 A | 10/1991 | Ensminger et al. |
| 5,059,186 A | 10/1991 | Yamamoto et al. |
| 5,069,206 A | 12/1991 | Crosbie |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |

(56) References Cited

U.S. PATENT DOCUMENTS

| | | | |
|---|---|---|---|
| 5,108,317 | A | 4/1992 | Beinhaur et al. |
| 5,108,375 | A | 4/1992 | Harrison et al. |
| 5,108,377 | A | 4/1992 | Cone et al. |
| 5,112,301 | A | 5/1992 | Fenton, Jr. et al. |
| 5,112,303 | A | 5/1992 | Pudenz et al. |
| 5,129,891 | A | 7/1992 | Young |
| 5,137,529 | A | 8/1992 | Watson et al. |
| 5,147,483 | A | 9/1992 | Melsky et al. |
| 5,152,753 | A | 10/1992 | Laguette et al. |
| 5,156,600 | A | 10/1992 | Young |
| 5,158,547 | A | 10/1992 | Doan et al. |
| 5,167,629 | A | 12/1992 | Vertenstein et al. |
| 5,167,633 | A | 12/1992 | Mann et al. |
| 5,167,638 | A | 12/1992 | Felix et al. |
| 5,169,393 | A | 12/1992 | Moorehead et al. |
| 5,171,228 | A | 12/1992 | McDonald |
| 5,176,653 | A | 1/1993 | Metals |
| 5,176,662 | A | 1/1993 | Bartholomew et al. |
| 5,178,612 | A | 1/1993 | Fenton, Jr. |
| 5,180,365 | A | 1/1993 | Ensminger et al. |
| 5,185,003 | A | 2/1993 | Brethauer |
| 5,189,690 | A | 2/1993 | Samuel |
| 5,193,106 | A | 3/1993 | DeSena |
| 5,195,122 | A | 3/1993 | Fabian |
| 5,195,123 | A | 3/1993 | Clement |
| 5,201,715 | A | 4/1993 | Masters |
| 5,201,722 | A | 4/1993 | Moorehead et al. |
| 5,203,771 | A | 4/1993 | Melker et al. |
| 5,203,777 | A | 4/1993 | Lee |
| 5,205,834 | A | 4/1993 | Moorehead et al. |
| 5,207,644 | A | 5/1993 | Strecker |
| 5,213,574 | A | 5/1993 | Tucker |
| 5,215,537 | A | 6/1993 | Lynn et al. |
| 5,222,499 | A | 6/1993 | Allen et al. |
| D337,637 | S | 7/1993 | Tucker |
| 5,224,938 | A | 7/1993 | Fenton, Jr. |
| 5,242,415 | A | 9/1993 | Kantrowitz et al. |
| 5,249,598 | A | 10/1993 | Schmidt |
| 5,263,930 | A | 11/1993 | Ensminger |
| D342,134 | S | 12/1993 | Mongeon |
| 5,281,199 | A | 1/1994 | Ensminger et al. |
| 5,281,205 | A | 1/1994 | McPherson |
| 5,290,263 | A | 3/1994 | Wigness et al. |
| 5,295,658 | A | 3/1994 | Atkinson et al. |
| 5,299,253 | A | 3/1994 | Wessels |
| 5,300,048 | A | 4/1994 | Drewes, Jr. et al. |
| 5,309,863 | A | 5/1994 | Leeb, Jr. |
| 5,312,337 | A | 5/1994 | Flaherty et al. |
| 5,318,545 | A | 6/1994 | Tucker |
| 5,320,100 | A | 6/1994 | Herweck et al. |
| 5,328,480 | A | 7/1994 | Melker et al. |
| 5,332,398 | A | 7/1994 | Miller et al. |
| 5,336,194 | A | 8/1994 | Polaschegg et al. |
| 5,338,398 | A | 8/1994 | Szwejkowski et al. |
| 5,350,360 | A | 9/1994 | Ensminger et al. |
| 5,352,204 | A | 10/1994 | Ensminger |
| 5,356,381 | A | 10/1994 | Ensminger et al. |
| 5,360,407 | A | 11/1994 | Leonard et al. |
| 5,383,223 | A | 1/1995 | Inokuchi |
| 5,383,233 | A | 1/1995 | Russell |
| 5,383,585 | A | 1/1995 | Weiss |
| 5,383,858 | A | 1/1995 | Reilly et al. |
| D355,240 | S | 2/1995 | Gladfelter et al. |
| 5,387,192 | A | 2/1995 | Glantz et al. |
| 5,394,457 | A | 2/1995 | Leibinger et al. |
| 5,395,324 | A | 3/1995 | Hinrichs et al. |
| 5,396,925 | A | 3/1995 | Poli |
| 5,397,329 | A | 3/1995 | Allen |
| 5,399,168 | A | 3/1995 | Wadsworth, Jr. et al. |
| 5,405,402 | A | 4/1995 | Dye et al. |
| 5,417,565 | A | 5/1995 | Long |
| 5,417,656 | A | 5/1995 | Ensminger et al. |
| 5,421,814 | A | 6/1995 | Geary |
| 5,423,334 | A | 6/1995 | Jordan |
| 5,425,762 | A | 6/1995 | Muller |
| 5,453,097 | A | 9/1995 | Paradis |
| 5,456,698 | A | 10/1995 | Byland et al. |
| 5,476,451 | A | 12/1995 | Ensminger et al. |
| 5,476,460 | A | 12/1995 | Montalvo |
| 5,476,880 | A | 12/1995 | Cooke et al. |
| 5,484,402 | A | 1/1996 | Saravia et al. |
| 5,503,630 | A | 4/1996 | Ensminger et al. |
| 5,507,813 | A | 4/1996 | Dowd et al. |
| 5,509,805 | A | 4/1996 | Jagmin |
| 5,513,637 | A | 5/1996 | Twiss et al. |
| 5,514,103 | A | 5/1996 | Srisathapat et al. |
| 5,520,632 | A | 5/1996 | Leveen et al. |
| 5,520,643 | A | 5/1996 | Ensminger et al. |
| 5,527,277 | A | 6/1996 | Ensminger et al. |
| 5,527,278 | A | 6/1996 | Ensminger et al. |
| 5,527,307 | A | 6/1996 | Srisathapat et al. |
| 5,531,684 | A | 7/1996 | Ensminger et al. |
| 5,542,923 | A | 8/1996 | Ensminger et al. |
| 5,545,143 | A | 8/1996 | Fischell |
| 5,554,117 | A | 9/1996 | Ensminger et al. |
| 5,556,381 | A | 9/1996 | Ensminger et al. |
| 5,558,641 | A | 9/1996 | Glantz et al. |
| 5,562,617 | A | 10/1996 | Finch, Jr. et al. |
| 5,562,618 | A | 10/1996 | Cai et al. |
| 5,575,770 | A | 11/1996 | Melsky et al. |
| 5,593,028 | A | 1/1997 | Haber et al. |
| 5,593,434 | A | 1/1997 | Williams |
| 5,607,393 | A | 3/1997 | Ensminger et al. |
| 5,607,407 | A | 3/1997 | Tolkoff et al. |
| 5,613,945 | A | 3/1997 | Cai et al. |
| 5,620,419 | A | 4/1997 | Lui et al. |
| 5,632,729 | A | 5/1997 | Cai et al. |
| 5,637,102 | A | 6/1997 | Tolkoff et al. |
| 5,638,832 | A | 6/1997 | Singer et al. |
| 5,647,855 | A | 7/1997 | Trooskin |
| RE35,601 | E | 9/1997 | Eckenhoff |
| 5,662,612 | A | 9/1997 | Niehoff |
| 5,662,616 | A | 9/1997 | Bousquet |
| 5,676,146 | A | 10/1997 | Scarborough |
| 5,695,490 | A | 12/1997 | Flaherty et al. |
| 5,702,128 | A | 12/1997 | Maxim et al. |
| 5,702,363 | A | 12/1997 | Flaherty |
| 5,704,915 | A | 1/1998 | Melsky et al. |
| 5,707,357 | A | 1/1998 | Mikhail et al. |
| 5,709,668 | A | 1/1998 | Wacks |
| 5,713,844 | A | 2/1998 | Peyman |
| 5,713,858 | A | 2/1998 | Heruth et al. |
| 5,713,859 | A | 2/1998 | Finch, Jr. et al. |
| 5,718,382 | A | 2/1998 | Jaeger |
| 5,718,682 | A | 2/1998 | Tucker |
| 5,725,507 | A | 3/1998 | Petrick |
| 5,733,336 | A | 3/1998 | Neuenfeldt et al. |
| 5,733,400 | A | 3/1998 | Gore et al. |
| 5,741,228 | A | 4/1998 | Lambrecht et al. |
| 5,743,873 | A | 4/1998 | Cai et al. |
| 5,743,891 | A | 4/1998 | Tolkoff et al. |
| 5,746,460 | A | 5/1998 | Marohl et al. |
| 5,755,780 | A | 5/1998 | Finch, Jr. et al. |
| 5,758,667 | A | 6/1998 | Slettenmark |
| 5,769,823 | A | 6/1998 | Otto |
| 5,773,552 | A | 6/1998 | Hutchings et al. |
| 5,776,188 | A | 7/1998 | Shepherd et al. |
| 5,792,104 | A | 8/1998 | Speckman et al. |
| 5,792,116 | A | 8/1998 | Berg et al. |
| 5,792,123 | A | 8/1998 | Ensminger |
| 5,797,886 | A | 8/1998 | Roth et al. |
| 5,810,789 | A | 9/1998 | Powers et al. |
| 5,814,016 | A | 9/1998 | Valley et al. |
| 5,824,071 | A | 10/1998 | Nelson et al. |
| 5,830,172 | A | 11/1998 | Leveen et al. |
| 5,833,654 | A | 11/1998 | Powers et al. |
| 5,835,563 | A | 11/1998 | Navab et al. |
| 5,836,935 | A | 11/1998 | Ashton et al. |
| 5,840,063 | A | 11/1998 | Flaherty |
| 5,843,069 | A | 12/1998 | Butler et al. |
| 5,848,989 | A | 12/1998 | Villani |
| 5,853,394 | A | 12/1998 | Tolkoff et al. |
| 5,868,702 | A | 2/1999 | Stevens et al. |
| 5,879,322 | A | 3/1999 | Lattin et al. |

(56) References Cited

U.S. PATENT DOCUMENTS

| | | | |
|---|---|---|---|
| 5,882,341 A | 3/1999 | Bousquet |
| 5,882,353 A | 3/1999 | VanBeek et al. |
| 5,895,424 A | 4/1999 | Steele, Sr. et al. |
| 5,897,528 A | 4/1999 | Schultz |
| 5,899,856 A | 5/1999 | Schoendorfer et al. |
| 5,904,934 A | 5/1999 | Maruyama et al. |
| 5,906,592 A | 5/1999 | Kriesel et al. |
| 5,906,596 A | 5/1999 | Tallarida |
| 5,908,413 A | 6/1999 | Lange et al. |
| 5,908,414 A | 6/1999 | Otto et al. |
| 5,911,706 A | 6/1999 | Estabrook et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,927,345 A | 7/1999 | Samson |
| 5,928,197 A | 7/1999 | Niehoff |
| 5,928,744 A | 7/1999 | Heilmann et al. |
| 5,931,829 A | 8/1999 | Burbank et al. |
| 5,941,856 A | 8/1999 | Kovacs et al. |
| 5,944,023 A | 8/1999 | Johnson et al. |
| 5,944,688 A | 8/1999 | Lois |
| 5,944,698 A | 8/1999 | Fischer et al. |
| 5,944,712 A | 8/1999 | Frassica et al. |
| D413,672 S | 9/1999 | Fogarty |
| 5,947,953 A | 9/1999 | Ash et al. |
| 5,951,512 A | 9/1999 | Dalton |
| 5,951,522 A | 9/1999 | Rosato et al. |
| 5,951,929 A | 9/1999 | Wilson |
| 5,954,687 A | 9/1999 | Baudino |
| 5,954,691 A | 9/1999 | Prosl |
| 5,957,890 A | 9/1999 | Mann et al. |
| 5,961,497 A | 10/1999 | Larkin |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,989,641 A | 11/1999 | Oulie |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,056,717 A | 5/2000 | Finch et al. |
| 6,077,756 A | 6/2000 | Lin et al. |
| 6,086,555 A | 7/2000 | Eliasen et al. |
| 6,090,066 A | 7/2000 | Schnell |
| 6,099,508 A | 8/2000 | Bousquet |
| 6,102,884 A | 8/2000 | Squitieri |
| 6,113,572 A | 9/2000 | Gailey et al. |
| 6,120,492 A | 9/2000 | Finch et al. |
| 6,152,909 A | 11/2000 | Bagaoisan et al. |
| 6,161,033 A | 12/2000 | Kuhn |
| 6,171,198 B1 | 1/2001 | Lizama Troncoso et al. |
| 6,171,298 B1 | 1/2001 | Matsuura et al. |
| 6,186,982 B1 | 2/2001 | Gross et al. |
| 6,190,352 B1 | 2/2001 | Haarala et al. |
| 6,193,684 B1 | 2/2001 | Burbank et al. |
| 6,198,807 B1 | 3/2001 | DeSena |
| 6,200,338 B1 | 3/2001 | Solomon et al. |
| 6,203,570 B1 | 3/2001 | Baeke |
| 6,210,366 B1 | 4/2001 | Sanfilippo, II |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,261,259 B1 | 7/2001 | Bell |
| 6,269,148 B1 | 7/2001 | Jessop et al. |
| 6,272,370 B1 | 8/2001 | Gillies et al. |
| 6,287,293 B1 | 9/2001 | Jones et al. |
| 6,290,677 B1 | 9/2001 | Arai et al. |
| 6,305,413 B1 | 10/2001 | Fischer et al. |
| 6,306,124 B1 | 10/2001 | Jones et al. |
| D450,115 S | 11/2001 | Bertheas |
| 6,332,874 B1 | 12/2001 | Eliasen et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,473,638 B2 | 10/2002 | Ferek-Petric |
| 6,475,516 B2 | 11/2002 | DiCosmo et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,562,023 B1 | 5/2003 | Marrs et al. |
| 6,572,583 B1 | 6/2003 | Olsen et al. |
| 6,582,418 B1 | 6/2003 | Verbeek et al. |
| 6,592,571 B1 | 7/2003 | Verbeek et al. |
| 6,610,031 B1 | 8/2003 | Chin |
| 6,613,002 B1 | 9/2003 | Clark et al. |
| 6,613,662 B2 | 9/2003 | Wark et al. |
| 6,626,936 B2 | 9/2003 | Stinson |
| D480,942 S | 10/2003 | Ishida et al. |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,663,646 B1 | 12/2003 | Shah |
| 6,676,633 B2 | 1/2004 | Smith et al. |
| 6,697,664 B2 | 2/2004 | Kienzle, III et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,726,063 B2 | 4/2004 | Stull et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,808,738 B2 | 10/2004 | DiTizio et al. |
| D498,894 S | 11/2004 | Gould |
| 6,826,257 B2 | 11/2004 | Sayre et al. |
| 6,827,709 B2 | 12/2004 | Fujii |
| 6,852,106 B2 | 2/2005 | Watson et al. |
| 6,878,136 B2 | 4/2005 | Fleury et al. |
| 6,878,137 B2 | 4/2005 | Benchetrit |
| 6,929,631 B1 | 8/2005 | Brugger et al. |
| 6,949,084 B2 | 9/2005 | Marggi et al. |
| 6,962,577 B2 | 11/2005 | Tallarida et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| D518,573 S | 4/2006 | French |
| 7,033,335 B2 | 4/2006 | Haarala et al. |
| 7,033,339 B1 | 4/2006 | Lynn |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,186,236 B2 | 3/2007 | Gibson et al. |

(56) References Cited

U.S. PATENT DOCUMENTS

| | | |
|---|---|---|
| 7,191,011 B2 | 3/2007 | Cantlon |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,252,469 B2 | 8/2007 | Zaluzec et al. |
| 7,252,649 B2 | 8/2007 | Sherry |
| 7,261,705 B2 | 8/2007 | Edoga et al. |
| D550,355 S | 9/2007 | Racz et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside et al. |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,442 S | 2/2008 | Blateri |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| D590,499 S | 4/2009 | Chesnin |
| 7,553,298 B2 | 6/2009 | Hunt et al. |
| D595,892 S | 7/2009 | Smith et al. |
| 7,563,025 B2 | 7/2009 | Kay |
| 7,658,196 B2 | 2/2010 | Ferreri et al. |
| D612,479 S | 3/2010 | Zawacki et al. |
| D613,394 S | 4/2010 | Linden |
| 7,713,251 B2 | 5/2010 | Tallarida et al. |
| D619,242 S | 7/2010 | Zinn et al. |
| 7,785,302 B2 | 8/2010 | Powers |
| D629,503 S | 12/2010 | Caffey et al. |
| 7,846,139 B2 | 12/2010 | Zinn et al. |
| D634,840 S | 3/2011 | Lombardi, III et al. |
| 7,909,804 B2 | 3/2011 | Stats |
| 7,947,022 B2 | 5/2011 | Amin et al. |
| 7,959,615 B2 | 6/2011 | Stats et al. |
| 7,972,314 B2 | 7/2011 | Bizup et al. |
| 8,021,324 B2 | 9/2011 | Bizup et al. |
| 8,025,639 B2 | 9/2011 | Powers et al. |
| 8,029,482 B2 | 10/2011 | Maniar et al. |
| D650,475 S | 12/2011 | Smith et al. |
| 8,075,536 B2 | 12/2011 | Gray et al. |
| 8,092,435 B2 | 1/2012 | Beling et al. |
| 8,147,455 B2 | 4/2012 | Butts et al. |
| 8,172,894 B2 | 5/2012 | Schmid et al. |
| 8,172,896 B2 | 5/2012 | McNamara et al. |
| 8,177,762 B2 | 5/2012 | Beasley et al. |
| 8,197,454 B2 | 6/2012 | Mann et al. |
| 8,202,259 B2 | 6/2012 | Evans et al. |
| 8,257,325 B2 | 9/2012 | Schweikert et al. |
| D676,955 S | 2/2013 | Orome |
| 8,382,723 B2 | 2/2013 | Powers et al. |
| 8,382,724 B2 | 2/2013 | Maniar et al. |
| 8,475,417 B2 | 7/2013 | Powers et al. |
| 2001/0016717 A1 | 8/2001 | Haarala et al. |
| 2001/0047165 A1 | 11/2001 | Makower et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0013557 A1 | 1/2002 | Sherry |
| 2002/0052576 A1 | 5/2002 | Massengale |
| 2002/0055715 A1 | 5/2002 | Young et al. |
| 2002/0095205 A1 | 7/2002 | Edwin et al. |
| 2002/0121530 A1 | 9/2002 | Socier |
| 2002/0138068 A1 | 9/2002 | Watson et al. |
| 2002/0169418 A1 | 11/2002 | Menzi et al. |
| 2002/0173769 A1 | 11/2002 | Gray et al. |
| 2002/0173772 A1 | 11/2002 | Olsen |
| 2002/0188282 A1 | 12/2002 | Greenberg |
| 2003/0028173 A1 | 2/2003 | Forsberg |
| 2003/0093029 A1 | 5/2003 | McGuckin et al. |
| 2003/0109856 A1 | 6/2003 | Sherry |
| 2003/0130627 A1 | 7/2003 | Smith et al. |
| 2003/0139812 A1 | 7/2003 | Garcia et al. |
| 2003/0141477 A1 | 7/2003 | Miller |
| 2003/0181878 A1 | 9/2003 | Tallarida et al. |
| 2003/0191452 A1 | 10/2003 | Meglin et al. |
| 2003/0208184 A1 | 11/2003 | Burke et al. |
| 2003/0216694 A1 | 11/2003 | Tollini |
| 2003/0217659 A1 | 11/2003 | Yamamoto et al. |
| 2004/0002693 A1 | 1/2004 | Bright et al. |
| 2004/0006316 A1 | 1/2004 | Patton |
| 2004/0020462 A1 | 2/2004 | Sauler et al. |
| 2004/0020492 A1 | 2/2004 | Dubrul et al. |
| 2004/0044306 A1 | 3/2004 | Lynch et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0078000 A1 | 4/2004 | Borchard et al. |
| 2004/0086568 A1 | 5/2004 | Ditizio et al. |
| 2004/0087877 A1 | 5/2004 | Besz et al. |
| 2004/0087885 A1 | 5/2004 | Kawano et al. |
| 2004/0106878 A1 | 6/2004 | Skujins et al. |
| 2004/0106891 A1 | 6/2004 | Langan et al. |
| 2004/0133173 A1 | 7/2004 | Edoga et al. |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0186444 A1 | 9/2004 | Daly et al. |
| 2004/0199129 A1 | 10/2004 | DiMatteo |
| 2004/0199220 A1 | 10/2004 | Cantlon |
| 2004/0204692 A1 | 10/2004 | Eliasen |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0010176 A1 | 1/2005 | Dikeman et al. |
| 2005/0027234 A1 | 2/2005 | Waggoner et al. |
| 2005/0027261 A1 | 2/2005 | Weaver et al. |
| 2005/0038390 A1 | 2/2005 | Fago et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0080401 A1 | 4/2005 | Peavey |
| 2005/0085778 A1 | 4/2005 | Parks |
| 2005/0113806 A1 | 5/2005 | De Carvalho et al. |
| 2005/0124980 A1 | 6/2005 | Sanders |
| 2005/0131352 A1 | 6/2005 | Conlon et al. |
| 2005/0148866 A1 | 7/2005 | Gunderson |
| 2005/0148869 A1 | 7/2005 | Masuda |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |

(56) References Cited

U.S. PATENT DOCUMENTS

| | | |
|---|---|---|
| 2006/0089619 A1 | 4/2006 | Ginggen |
| 2006/0100592 A1 | 5/2006 | Eliasen |
| 2006/0116648 A1 | 6/2006 | Hamatake |
| 2006/0171980 A1 | 8/2006 | Helmus et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0217668 A1 | 9/2006 | Schulze et al. |
| 2006/0224128 A1 | 10/2006 | Lurvey et al. |
| 2006/0224129 A1 | 10/2006 | Beasley et al. |
| 2006/0241465 A1 | 10/2006 | Huennekens et al. |
| 2006/0247584 A1 | 11/2006 | Sheetz et al. |
| 2006/0253076 A1 | 11/2006 | Butts et al. |
| 2006/0264898 A1 | 11/2006 | Beasley et al. |
| 2007/0003603 A1 | 1/2007 | Karandikar et al. |
| 2007/0007839 A1 | 1/2007 | Lin |
| 2007/0010881 A1 | 1/2007 | Soye et al. |
| 2007/0016162 A1 | 1/2007 | Burbank et al. |
| 2007/0049806 A1 | 3/2007 | Adams et al. |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083111 A1 | 4/2007 | Hossack et al. |
| 2007/0083156 A1 | 4/2007 | Muto et al. |
| 2007/0100302 A1 | 5/2007 | Dicarlo et al. |
| 2007/0112332 A1 | 5/2007 | Harding et al. |
| 2007/0120683 A1 | 5/2007 | Flippen et al. |
| 2007/0123831 A1 | 5/2007 | Haindl et al. |
| 2007/0135775 A1 | 6/2007 | Edoga et al. |
| 2007/0149920 A1 | 6/2007 | Michels et al. |
| 2007/0149921 A1 | 6/2007 | Michels et al. |
| 2007/0149947 A1 | 6/2007 | Byrum |
| 2007/0161958 A1 | 7/2007 | Glenn |
| 2007/0179456 A1 | 8/2007 | Glenn |
| 2007/0185462 A1 | 8/2007 | Byrum |
| 2007/0191773 A1 | 8/2007 | Wojcik |
| 2007/0207335 A1 | 9/2007 | Karandikar et al. |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0255226 A1 | 11/2007 | Tennican et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0276355 A1 | 11/2007 | Nielsen et al. |
| 2007/0282308 A1 | 12/2007 | Bell |
| 2007/0293800 A1 | 12/2007 | McMaken et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0108949 A1 | 5/2008 | Beasley et al. |
| 2008/0114308 A1 | 5/2008 | di Palma et al. |
| 2008/0133265 A1 | 6/2008 | Silkaitis et al. |
| 2008/0137923 A1 | 6/2008 | Spahn |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0204072 A1 | 8/2009 | Amin et al. |
| 2009/0204074 A1 | 8/2009 | Powers et al. |
| 2009/0216216 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2009/0227964 A1 | 9/2009 | DiCarlo et al. |
| 2009/0322541 A1 | 12/2009 | Jones et al. |
| 2010/0010339 A1 | 1/2010 | Smith et al. |
| 2010/0042073 A1 | 2/2010 | Oster et al. |
| 2010/0063451 A1 | 3/2010 | Gray et al. |
| 2010/0069743 A1 | 3/2010 | Sheetz et al. |
| 2010/0106094 A1 | 4/2010 | Fisher et al. |
| 2010/0121283 A1 | 5/2010 | Hamatake et al. |
| 2010/0211026 A2 | 8/2010 | Mr. Sheetz et al. |
| 2010/0268174 A1 | 10/2010 | Steinke et al. |
| 2011/0021922 A1 | 1/2011 | Berard-Anderson et al. |
| 2011/0092921 A1 | 4/2011 | Beling et al. |
| 2011/0098662 A1 | 4/2011 | Zinn |
| 2011/0098663 A1 | 4/2011 | Zinn |
| 2011/0118677 A1 | 5/2011 | Wiley et al. |
| 2011/0183712 A1 | 7/2011 | Eckstein et al. |
| 2011/0213700 A1 | 9/2011 | Sant'Anselmo |
| 2011/0257609 A1 | 10/2011 | Bizup et al. |
| 2011/0264058 A1 | 10/2011 | Linden et al. |
| 2011/0271856 A1 | 11/2011 | Fisher et al. |
| 2011/0275930 A1 | 11/2011 | Jho et al. |
| 2011/0276015 A1 | 11/2011 | Powers et al. |
| 2011/0288502 A1 | 11/2011 | Hibdon et al. |
| 2011/0288503 A1 | 11/2011 | Magalich et al. |
| 2011/0311337 A1 | 12/2011 | Amin et al. |
| 2012/0018073 A1 | 1/2012 | Maniar et al. |
| 2012/0059250 A1 | 3/2012 | Gray et al. |
| 2012/0065622 A1 | 3/2012 | Cornish et al. |
| 2012/0078201 A1 | 3/2012 | Mikami |
| 2012/0078202 A1 | 3/2012 | Beling et al. |
| 2012/0191071 A1 | 7/2012 | Butts et al. |
| 2012/0259296 A1 | 10/2012 | Sheetz et al. |
| 2012/0302969 A1 | 11/2012 | Wiley et al. |
| 2013/0165773 A1 | 6/2013 | Powers et al. |
| 2013/0172733 A1 | 7/2013 | Maniar et al. |

FOREIGN PATENT DOCUMENTS

| | | |
|---|---|---|
| CA | 2692142 A1 | 12/2008 |
| CA | 2693972 A1 | 1/2009 |
| CN | 102421469 A | 4/2012 |
| CN | 102612343 A | 7/2012 |
| DE | 3618390 C1 | 11/1987 |
| DE | 3720414 A1 | 12/1987 |
| DE | 42 25 524 A1 | 2/1994 |
| DE | 29512576 U1 | 10/1995 |
| DE | 10346470 A1 | 5/2005 |
| EP | 0128525 A2 | 12/1984 |
| EP | 0134745 A1 | 3/1985 |
| EP | 0343910 A2 | 11/1989 |
| EP | 0366814 A1 | 5/1990 |
| EP | 0619101 A1 | 10/1994 |
| EP | 1238682 A2 | 9/2002 |
| EP | 1635899 A2 | 3/2006 |
| EP | 2006019101 A2 | 12/2006 |
| EP | 1858565 A1 | 11/2007 |
| EP | 1874393 A1 | 1/2008 |
| EP | 1896117 A2 | 3/2008 |
| EP | 1998842 A2 | 12/2008 |
| EP | 2004272 A2 | 12/2008 |
| EP | 2018209 A2 | 1/2009 |
| EP | 2081634 A1 | 7/2009 |
| EP | 2164559 A1 | 3/2010 |
| EP | 2167182 A1 | 3/2010 |
| EP | 2180915 A1 | 5/2010 |
| EP | 2190517 A1 | 6/2010 |
| EP | 2308547 A2 | 4/2011 |
| EP | 2320974 A1 | 5/2011 |
| EP | 2324878 A2 | 5/2011 |

(56) References Cited

FOREIGN PATENT DOCUMENTS

| | | |
|---|---|---|
| EP | 2324879 A2 | 5/2011 |
| EP | 2324880 A2 | 5/2011 |
| EP | 2365838 A1 | 9/2011 |
| EP | 2571563 A1 | 3/2013 |
| FR | 2508008 A1 | 12/1982 |
| FR | 2809315 A1 | 11/2001 |
| GB | 966137 A | 8/1964 |
| GB | 2102398 A | 2/1983 |
| JP | 62155857 A | 7/1987 |
| JP | 62281966 A | 12/1987 |
| JP | 6296633 A | 10/1994 |
| JP | 2000-079168 A | 3/2000 |
| JP | 2002500076 A | 1/2002 |
| JP | 2003-510136 A | 3/2003 |
| JP | 2006025948 A | 2/2006 |
| JP | 2012-523284 A | 10/2012 |
| JP | 2013-510652 | 3/2013 |
| JP | 2013-526376 A | 6/2013 |
| WO | 8600213 A1 | 1/1986 |
| WO | 8911309 A1 | 11/1989 |
| WO | 9001958 A1 | 3/1990 |
| WO | 9206732 A1 | 4/1992 |
| WO | 9305730 A1 | 4/1993 |
| WO | 9308986 A1 | 5/1993 |
| WO | 9405351 A1 | 3/1994 |
| WO | 9516480 A1 | 6/1995 |
| WO | 9701370 A1 | 1/1997 |
| WO | 9706845 A1 | 2/1997 |
| WO | 9711726 A1 | 4/1997 |
| WO | 9723255 A1 | 7/1997 |
| WO | 9726931 A1 | 7/1997 |
| WO | 9817337 A1 | 4/1998 |
| WO | 9818506 A1 | 5/1998 |
| WO | 9831417 A2 | 7/1998 |
| WO | 9934859 A1 | 7/1999 |
| WO | 9938553 A1 | 8/1999 |
| WO | 9942166 A1 | 8/1999 |
| WO | 0012171 A1 | 3/2000 |
| WO | 0016844 A1 | 3/2000 |
| WO | 0033901 A1 | 6/2000 |
| WO | 0123023 A1 | 4/2001 |
| WO | 0160444 A1 | 8/2001 |
| WO | 0247549 A1 | 6/2002 |
| WO | 03084832 A1 | 10/2003 |
| WO | 03090509 A2 | 11/2003 |
| WO | 2004004800 A2 | 1/2004 |
| WO | 2004028611 A1 | 4/2004 |
| WO | 2004071555 A2 | 8/2004 |
| WO | 2004091434 A2 | 10/2004 |
| WO | 2005037055 A2 | 4/2005 |
| WO | 2005068009 A1 | 7/2005 |
| WO | 2006078915 A2 | 7/2006 |
| WO | 2006096686 A1 | 9/2006 |
| WO | 2006116438 A1 | 11/2006 |
| WO | 2006116613 A1 | 11/2006 |
| WO | 2006130133 A1 | 12/2006 |
| WO | 2006134100 A1 | 12/2006 |
| WO | 2007041471 A2 | 4/2007 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008019236 A1 | 2/2008 |
| WO | 2008048361 A1 | 4/2008 |
| WO | 2008062173 A1 | 5/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |
| WO | 2009012385 A1 | 1/2009 |
| WO | 2009012395 A1 | 1/2009 |
| WO | 2009035582 A1 | 3/2009 |
| WO | 2009046439 A2 | 4/2009 |
| WO | 2009046725 A1 | 4/2009 |
| WO | 2009108669 A1 | 9/2009 |
| WO | 2010030351 A1 | 3/2010 |
| WO | 2010062633 A1 | 6/2010 |
| WO | 2010118144 A1 | 10/2010 |
| WO | 2011046604 A2 | 4/2011 |
| WO | 2011053499 A1 | 5/2011 |
| WO | 2011056619 A1 | 5/2011 |
| WO | 2011062750 A1 | 5/2011 |
| WO | 2011133950 A1 | 10/2011 |
| WO | 2011146649 A1 | 11/2011 |

OTHER PUBLICATIONS

PCT/US2008/070330 filed Jul. 17, 2008 Written Opinion dated Dec. 1, 2008.
PCT/US2008/070345 filed Jul. 17, 2008 Search Report mailed on Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/062854 filed Oct. 30, 2009 International Search Report dated Dec. 10, 2009.
PCT/US2009/062854 filed Oct. 30, 2009 Written Opinion dated Dec. 10, 2009.
Port-A-Cath® P.A.S. PORT® Systems by Deltec, Product Specifications, 1999.
PORT-A-CATH® "Implantable Epidural, Aterial and Peritonial Access Systems" Internet Product Listing. <<http://web.archive.org/web/20001119035900/www.deltec.com/cPacspl.htm.>> last accessed Jun. 4, 2012.
PORT-A-CATH® "Many PORT-A-CATH® System Choices" Product Brochure. © 1996 SIMS Deltec, Inc.
Rappolt, Richard T., et al. "Radiopaque Codification and X-ray Identification of Ingested Drugs." Ingestive Radiology, May-Jun. 1966.
Sandstede, Joern, "Pediatric CT," available online at www.multislice-ct.com, MultiSLICE-CT.com, version 02, May 2, 2003.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith Medical, PORT-A-CATH® "Single-lumen Implantable Vascular Access Systems" Product Specifications, 2004.
Smith, Lisa Hartkoph, "Implanted Ports, Computed Tomography, Power Injectors, and Catheter Rupture." Clinical Journal of Oncology Nursing, vol. 12 , No. 5. Oct. 2008.
Soloman, et al., "CIN Strategies: Anticipate, Manage, Prevent." Supplement to Imaging Economics, May 2007.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.

(56) References Cited

OTHER PUBLICATIONS

U.S. Appl. No. 10/374,000, filed Feb. 25, 2003 Non-final Office Action mailed Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action mailed Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/368,954, filed Mar. 6, 2006 Non-Final Office Action dated Jul. 21, 2009.
U.S. Appl. No. 11/368,954, filed Mar. 6, 2006 Final Office Action dated Jan. 27, 2010.
U.S. Appl. No. 11/368,954, filed Mar. 6, 2006 Supplemental Non-final Office Action mailed Oct. 2, 2009.
U.S. Appl. No. 11/380,124, filed Apr. 25, 2006 Final Office Action dated Sep. 21, 2009.
U.S. Appl. No. 11/380,124, filed Apr. 25, 2006 Non-Final Office Action dated Apr. 26, 2010.
U.S. Appl. No. 11/380,124, filed Apr. 25, 2006 Non-Final Office Action dated Jan. 16, 2009.
U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action issued on Dec. 3, 2008.
U.S. Appl. No. 11/725,287, filed Mar. 19, 2007 Non-final Office Action issued on Jun. 12, 2009.
Allergan, Inc. LAP-BAND® System Fact Sheet. © 2007.
BARD Access Systems Mar. 21, 1995 Product Release to Market form for "M.R.I. Port with 8 Fr. ChronoFlexÒ Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit". Drawings included.
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.
BioEnterics Corporation, LAP-BAND® "Adjustable Gastric Banding System" Product Brochure.

Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Costa, Nancy, "More Than Skin Deep: An Overview of Iodinated Contrast Media.." Journal for the Association for Vascular Access, vol. 8, No. 4, 2003.
Costa, Nancy, "Understanding Contrast Media." Journal of Infusion Nursing, vol. 27, No. 5, Sep./Oct. 2004.
EP 06751411 filed Apr. 25, 2006 Office Action dated Sep. 2, 2008.
EP 99964086 filed Dec. 3, 1999 Office Action dated Dec. 15, 2005.
EP 99964086 filed Dec. 3, 1999 Office Action dated Mar. 1, 2005.
EP 99964086 filed Dec. 3, 1999 Office Action dated Mar. 30, 2005.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
Hou, Shaw-Min et al. "Comparisons of Outcomes and Survivals for Two Central Venous Access Port Systems." Journal of Surgical Oncology, 91:61-66, 2005.
Inamed Health, BioEnterics® LAP-BAND® "Adjustable Gastric Banding System" Product Brochure, Dec. 2003.
Johnson, Kathleen A., "Power Injectable Portal Systems." Journal of Radiology Nursing, vol. 28, Issue 1, Mar. 2009.
LaMaitre Vascular "Port Implantations: using the OptiLock Implantable Port," product information, available at http://www.lemaitre.com/specs.pop.asp, last accessed Apr. 2003, 14 pages.
LAP-BAND AP™ "System with Adjustable Gastric Banding system with OMNIFORM TN Design," Product Brochure, Jul. 2007, 16 pages.
LAP-BAND® System Access Port Fill Guide I, "9.75/10.0 cm LAP-BAND System vs. 11 cm LAP-BAND System: For Product Manufactured Prior to Jul. 2001" BioEnterics Corporation.
MedComp "PortCT Technology", display at SIR Conference (Mar. 2006), Toronto, Canada.
Nucleus Cochlear Implant Systems; User Manual for the ESPrit 3G speech processor and accessories, Issue 2, Dec. 2001 http://www.cochlearamericas.com/PDFs/UserManualSprint.pdf.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PCT/US1999/028695 filed Dec. 3, 1999 International Preliminary Examination Report dated Apr. 21, 2001.
PCT/US1999/028695 filed Dec. 3, 1999 Search Report dated Apr. 11, 2000.
PCT/US2006/008022 filed Mar. 6, 2006 International Preliminary Report on Patentability dated Sep. 12, 2007.
PCT/US2006/008022 filed Mar. 6, 2006 Search Report dated Jul. 5, 2006.
PCT/US2006/008022 filed Mar. 6, 2006 Written Opinion dated Apr. 9, 2007.
PCT/US2006/015695 filed Apr. 25, 2006 Partial Search Report dated Sep. 29, 2006.
PCT/US2006/015695 filed Apr. 25, 2006 Search Report dated Jan. 11, 2007.
PCT/US2006/015695 filed Apr. 25, 2006 Written Opinion dated Jan. 11, 2007.
PCT/US2006/016056 filed Apr. 27, 2006 International Preliminary Report on Patentability dated Oct. 30, 2007.
PCT/US2006/016056 filed Apr. 27, 2006 Search Report dated Sep. 20, 2006.
PCT/US2006/016056 filed Apr. 27, 2006 Written Opinion dated Oct. 27, 2007.
PCT/US2006/049007 filed Dec. 21, 2006 International Preliminary Report on Patentability dated Jul. 1, 2008.
PCT/US2006/049007 filed Dec. 21, 2006 Search Report dated Oct. 1, 2007.

(56) References Cited

OTHER PUBLICATIONS

PCT/US2007/006776 filed Mar. 19, 2007 International Preliminary Report on Patentability dated Jan. 2, 2009.
PCT/US2007/006776 filed Mar. 19, 2007 Search Report, dated Dec. 18, 2007.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Oct. 29, 2008.
PCT/US2007/011015 filed May 7, 2007 Search Report dated Jun. 10, 2008.
PCT/US2007/011456 filed May 11, 2007 Search Report dated Aug. 28, 2008.
PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion mailed on Sep. 30, 2008.
AngioDynamics, Smart Port Guidelines for Health Care Providers, 1996.
B. Braun, Easypump Product Page, accessed May 11, 2011.
B. Braun, Port Catheter Systems Product Page, accessed May 11, 2011.
Bard Healthcare Leaflet (2001).
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Braun Product Catalog (Aug. 2005).
Carlson et al., "Safety Considerations in the Power Injection of Contrast Media Via Central Venous Catheters during Computed Tomographic Examinations," Investigative Radiology, (May 1992) 27: 337-340.
Clinical Plastic Products, "Oncology Jet Port Plus Catheter Systems" Instructions for Use, 2011.
Cook Vital-Port® Product Catalog (2000).
Coyle, Douglas et al, Power Injection of Contrast Media via Peripherally Inserted Central Catheters for CT, J Vasc Intern Radiol, pp. 809-814, vol. 15, 2004.
Deltec Port Systems (Feb. and Apr. 1996).
Department of Health and Human Services, C-Port 510(k) FDA Clearance, Jun. 5, 2003.
EP 06751411 filed Apr. 25, 2006 Office Action dated Aug. 10, 2009.
EP 06751411 filed Apr. 25, 2006 Opposition by Aesculap AG dated Oct. 5, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 12, 2011.
EP 06845998 filed Dec. 21, 2006 Office Action dated Mar. 10, 2011.
EP 06845998 filed Dec. 21, 2006 Supplementary Search Report dated Jul. 22, 2010.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
JP 2007-558331 filed Mar. 6, 2006 Office Action dated May 17, 2011.
JP 2008-509056 filed Apr. 25, 2006 Office Action dated Apr. 4, 2012.
JP 2008-509056 filed Apr. 25, 2006 Office Action dated Jun. 7, 2011.

Kaste et al., "Safe use of power injectors with central and peripheral venous access devices for pediatric CT," Pediatr Radiol (1996) 26: 499-501.
L-CATH® For Ports, Luther Medical Products, Inc., Tustin, California, 2 pages, 1994.
Leslie et al., "A New Simple Power Injector," Am J Roentgenol 128: 381-384, Mar. 1977.
Navilyst Medical, Implantable Ports with PASV® Valve Technology, Product Overview,<<http://www.navilystmedical.com/Products/index.cfm/9>> last accessed Jun. 4, 2012.
PCT/US2006/008022 filed Mar. 6, 2006 Written Opinion dated Jul. 5, 2006.
PCT/US2006/016056 filed Apr. 27, 2006 Written Opinion dated Sep. 20, 2006.
PCT/US2006/049007 filed Dec. 21, 2006 Written Opinion dated Oct. 1, 2007.
PCT/US2009/035088 filed Feb. 25, 2009 International Search Report dated May 19, 2009.
PCT/US2009/035088 filed Feb. 25, 2009 Written Opinion dated May 19, 2009.
PCT/US2009/062854 filed Oct. 30, 2009 International Preliminary Report on Patentability dated May 5, 2011.
PCT/US2009/062854 filed Oct. 30, 2009 Search Report dated Dec. 23, 2009.
PCT/US2009/062854 filed Oct. 30, 2009 Written Opinion dated Dec. 23, 2009.
PCT/US2010/030256 filed Apr. 7, 2010 Search Report and Written Opinion dated Jun. 4, 2010.
PCT/US2010/030256 filed Apr. 7, 2010 Search Report dated Jun. 4, 2010.
PCT/US2010/030256 filed Apr. 7, 2010 Written Opinion dated Jun. 4, 2010.
PCT/US2010/054994 filed Nov. 1, 2010 Search Report dated Jan. 10, 2011.
PCT/US2010/054994 filed Nov. 1, 2010 Written Opinion dated Jan. 10, 2011.
PORT-A-CATH® & PORT-A-CATH® II Dual-lumen Implantable Venous Access Systems Product Specifications, 2005.
PORT-A-CATH® and P.A.S. PORT® Power P.A.C. Information Sheet, 2006.
U.S. Appl. No. 11/725,287, filed Mar. 19, 2007 Non-final Office Action issued on Mar. 29, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/143,377, filed Jun. 20, 2008 Final Office Action mailed Oct. 19, 2009.
U.S. Appl. No. 12/143,377, filed Jun. 20, 2008 Non-final Office Action mailed Apr. 27, 2009.
U.S. Appl. No. 12/175,182, filed Jul. 17, 2008 Non-final Office Action mailed Sep. 3, 2009.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jun. 30, 2009.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.

(56) References Cited

OTHER PUBLICATIONS

U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annmarie Boswell as inventors.
Vergara, et al., "Adverse Reactions to Contrast Medica in CT: Effects of Temperature and Ionic Property." Radiology, vol. 199, No. 2, May 1996.
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
Salis et al., "Maximal flow rates possible during power injection through currently available PICCs: An in-vitro study," J Vasc Intery Radiol 2004; 15:275-281.
Smiths Medical, "Smiths Medical Launches Implantable Ports for Easy Viewing Under CT Scans" Press Release, Jan. 5, 2011.
Statement of Prof. Dr. med. Karl R. Aigner, Oct. 11, 2011.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.
U.S. Appl. No. 11/368,954, filed Mar. 6, 2006 Notice of Allowance dated Jun. 24, 2010.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Oct. 20, 2011.
U.S. Appl. No. 11/380,124, filed Apr. 25, 2006 Non-Final Office Action dated Apr. 7, 2011.
U.S. Appl. No. 11/380,124, filed Apr. 25, 2006 Non-Final Office Action dated Oct. 28, 2010.
U.S. Appl. No. 11/380,621, filed Apr. 27, 2006 Final Office Action dated Mar. 8, 2011.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Non-Final Office Action dated Dec. 13, 2010.
U.S. Appl. No. 12/023,280, filed Jan. 31, 2008 Notice of Allowance dated Mar. 28, 2011.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Aug. 5, 2011.
U.S. Appl. No. 12/419,854, filed Apr. 7, 2009 Non-Final Office Action dated Jun. 26, 2012.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Notice of Allowance dated Mar. 7, 2011.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Advisory Action dated Sep. 15, 2011.
U.S. Appl. No. 12/617,981, filed Nov. 13, 2009 Final Office Action dated Aug. 2, 2012.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Dec. 21, 2011.
U.S. Appl. No. 12/617,981, filed Nov. 13, 2009 Non-Final Office Action dated Jan. 5, 2011.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 13/113,834, filed May 23, 2011 Non-Final Office Action dated Jul. 17, 2012.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
Wikipedia, "Port Catheter", Dec. 15, 2011.
Bard Access Systems, BardPort and X-Port Implanted Ports Brochure, © 2007.
Bard Access Systems, BardPort, Slim Port and X-Port Instructions for Use, May 2003.
Bard Access Systems, BardPort™ Implanted Ports Patient Information, Feb. 1993.
Bard Access Systems, Ports Brochure, © 2003.
Bard Access Systems, Titanium Dome Implantable Port, http://www.bardacess.com, last accessed Jan. 10, 2012.
CN 200980153471.3 filed Jun. 30, 2011 First Office Action dated Dec. 25, 2012.
EP 06751411 filed Apr. 25, 2006 Decision Revoking the European Patent dated Aug. 1, 2012.
EP 06845998.1 filed Dec. 21, 2006 Examination Report dated Nov. 7, 2012.
EP 10762377.9 filed Oct. 5, 2011 European Search Report dated Aug. 3, 2012.
JP 2007-558331 filed Mar. 6, 2006 Office Action dated Jan. 22, 2013.
Medtronic IsoMed® Constant-Flow Infusion System: Clinical Reference Guide for Hepatic Arterial Infusion Therapy, Revised Sep. 2000.
Nucleus Cochlear Implant Systems; User Manual for the ESPrit and ESPrit 22 speech processor and accessories, Issue 3, Apr. 2000.
PCT/US11/37038 filed May 18, 2011 Written Opinion and Search Report dated Aug. 30, 2011.
PCT/US2011/037038 filed May 18, 2011 International Preliminary Report on Patentability dated Nov. 29, 2012.
PCT/US2011/037038 filed May 18, 2011 International Search Report and Written Opinion dated Aug. 30, 2011.

(56) References Cited

OTHER PUBLICATIONS

Request for Inter partes Reexamination of U.S. Patent No. 7,785,302, filed Aug. 20, 2012.
Request for Inter partes Reexamination of U.S. Patent No. 7,947,022, filed Aug. 20, 2012.
Request for Inter partes Reexamination of U.S. Patent No. 7,959,615, filed Aug. 20, 2012.
U.S. Appl. No. 11/937,302, filed Nov. 8, 2007 Final Office Action dated Nov. 8, 2012.
U.S. Appl. No. 12/267,160, filed Nov. 7, 2008 Examiner's Answer dated Dec. 5, 2012.
U.S. Appl. No. 12/420,007, filed Apr. 7, 2009 Non-Final Office Action dated Oct. 16, 2012.
U.S. Appl. No. 12/917,323, filed Nov. 1, 2010 Final Office Action dated Jan. 29, 2013.
U.S. Appl. No. 12/917,323, filed Nov. 1, 2010 Non-Final Office Action dated Aug. 15, 2012.
U.S. Appl. No. 13/113,834, filed May 23, 2011 Final Office Action dated Nov. 23, 2012.
U.S. Appl. No. 13/438,586, filed Apr. 3, 2012 Non-Final Office Action dated Sep. 19, 2012.
U.S. Appl. No. 29/382,235, filed Dec. 30, 2010 Non-Final Office Action dated Oct. 3, 2012.
U.S. Appl. No. 29/382,246, filed Dec. 30, 2010 Notice of Allowance dated Oct. 3, 2012.
U.S. Appl. No. 95/002,089 filed Aug. 20, 2012 Office Action in and Order Granting/Denying Request for Inter Partes Reexamination dated Nov. 7, 2012.
US 95/002,090, filed Aug. 20, 2012 Office Action in and Order Granting/Denying Request for Inter Partes Reexamination dated Nov. 7, 2012.
US 95/002,092, filed Aug. 20, 2012 Office Action in and Order Granting/Denying Request for Inter Partes Reexamination dated Nov. 13, 2012.
CN 201080020088.3 filed Nov. 7, 2011 First Office Action dated Mar. 4, 2013.
EP 06751664.1 filed Apr. 27, 2006 First Examination Report dated Jul. 11, 2013.
EP 06845998.1 filed Dec. 21, 2006 Examination Report dated May 13, 2013.
EP 10183380.4 filed Apr. 25, 2006 European Search Report dated May 22, 2013.
EP 10183382.0 filed Apr. 25, 2006 European Search Report dated May 22, 2013.
EP 10183394.5 filed Apr. 25, 2006 European Search Report dated May 22, 2013.
EP 10183398.6 filed Apr. 25, 2006 European Search Report dated May 22, 2013.
EP 10762377.9 filed Oct. 5, 2011 Office Action dated Jul. 17, 2013.
EP 13158343.7 filed Mar. 8, 2013 Extended European Search Report dated May 14, 2013.
Ethanol Lock Technique for Prevention and Treatment of Central line-Associated Bloodstream Infections (Nebraska) Aug. 13, 2011, Accessed: Jun. 29, 2013 http://www.nebraskamed.com/app_files/pdf/careers/education-programs/asp/tnmc_etohlock_final.pdf.
JP 2012-156976 filed Jul. 12, 2012 Submission of Documents by Third Party dated May 14, 2013.
Medcomp Dialysis and Vascular Access Products (MEDCOMP) Jun. 30, 2009, Accessed Jun. 29, 2013 http://www.medcompnet.com/products/flipbook/pdf/PN2114G_Medcomp_Catalog.pdf.
PCT/US2013/031035 filed Mar. 13, 2013 International Search Report and Written Opinion dated Jun. 3, 2013.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
U.S. Appl. No. 11/380,124, filed Apr. 25, 2006 Notice of Allowance dated Apr. 29, 2013.
U.S. Appl. No. 12/419,854, filed Apr. 7, 2009 Advisory Action dated May 17, 2013.
U.S. Appl. No. 12/419,854, filed Apr. 7, 2009 Final Office Action dated Feb. 14, 2013.
U.S. Appl. No. 12/420,007, filed Apr. 7, 2009 Final Office Action dated Mar. 22, 2013.
U.S. Appl. No. 12/917,323, filed Nov. 1, 2010 Advisory Action dated Apr. 10, 2013.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/571,088, filed Aug. 9, 2012 Final Office Action dated Jul. 16, 2013.
U.S. Appl. No. 13/571,088, filed Aug. 9, 2012 Non-Final Office Action dated Feb. 27, 2013.
U.S. Appl. No. 13/776,451, filed Feb. 25, 2013 Non-Final Office Action dated Jul. 24, 2013.
U.S. Appl. No. 13/853,942, filed Mar. 29, 2013 Non-Final Office Action dated Jul. 26, 2013.

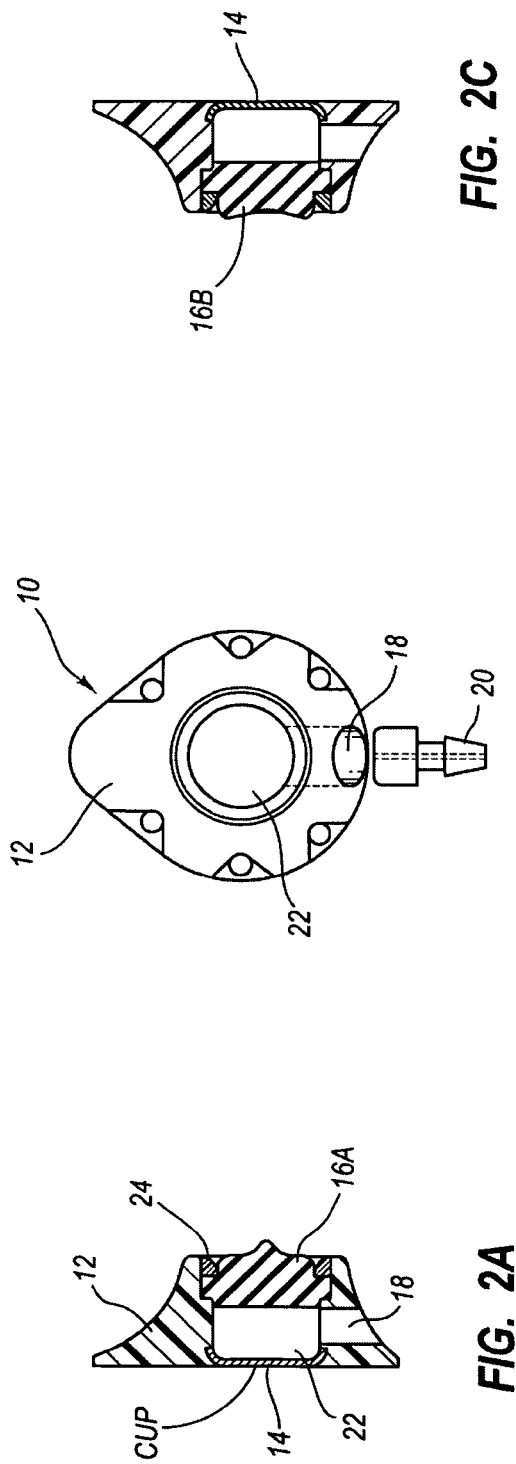

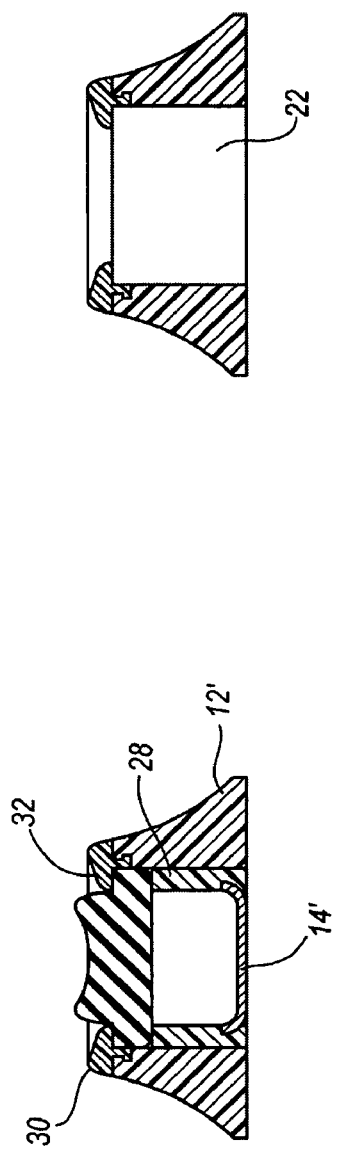
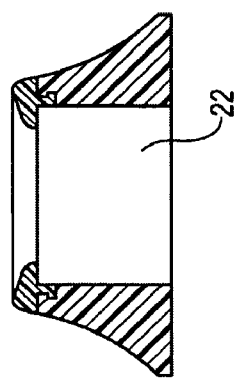
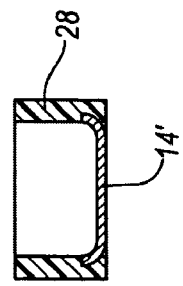
FIG. 3A
FIG. 3B
FIG. 3C
FIG. 3D

SEPTUM FEATURE FOR IDENTIFICATION OF AN ACCESS PORT

CROSS-REFERENCE TO RELATED APPLICATIONS

This application is a continuation of U.S. patent application Ser. No. 11/320,223, filed Dec. 28, 2005, now U.S. Pat. No. 8,177,762, which claims the benefit of priority to U.S. Provisional Patent Application No. 60/658,518, filed Mar. 4, 2005, and which is a continuation-in-part of U.S. patent application Ser. No. 10/374,000, filed Feb. 25, 2003, now U.S. Pat. No. 7,713,251, which is a continuation of U.S. patent application Ser. No. 09/582,406, filed Jun. 23, 2000, now U.S. Pat. No. 6,527,754, which is a U.S. national stage application under 35 USC §371 of International Application No. PCT/US99/28695, filed Dec. 3, 1999, which claims the benefit of priority to U.S. Provisional Patent Application No. 60/111,257, filed Dec. 7, 1998, the disclosure of each of which is incorporated, in its entirety, by this reference.

BACKGROUND

Access portals, or ports, provide a convenient method to repeatedly deliver medicants to remote areas of the body without utilizing surgical procedures. The port is totally implantable within the body, and permits the infusion of medications, parenteral solutions, blood products, and other fluids. The port may also be used for blood sampling Known ports typically include a chamber accessible through a self-sealing septum. Septums of the prior art vary in shape, from a wafer-like cylindrical block of silicone to a pre-molded septum of U.S. Pat. No. 4,802,885 to Weeks et al. The pre-molded septum of U.S. Pat. No. 4,802,885 includes opposed convex surfaces and a peripheral ledge.

In common practice, a caregiver locates the septum of the port by palpation. Port access is accomplished by percutaneously inserting a needle, typically a non-coring needle, perpendicularly through the septum of the port and into the chamber. The drug or fluid is then administered by bolus injection or continuous infusion. Ordinarily the fluid flows through the chamber, into a catheter and finally to the site where the fluid is desired. Except for the septum, traditional ports are constructed from all-metal or all-plastic. Each type of construction has unique advantages and disadvantages.

All-metal constructions have the advantages that they maintain a septum in a self-sealing fashion after repeated percutaneous injections. Additionally, all-metal constructions, such as titanium, or stainless steel provide a port which is both biocompatible and compatible with the injected fluid.

However, all-metal constructions present the disadvantages that they are relatively heavy, difficult to fabricate and relatively expensive. Additionally, all-metal ports produce large Magnetic Resonance Imaging (MRI) artifacts. On the other hand, all-plastic ports have the advantages that they are inexpensive to construct, light in weight, and do not create an MRI artifact. However, ports constructed from plastic have the disadvantage that infused fluids may react with the plastic body of the port. All-plastic ports contain the disadvantage that they cannot maintain a sealing engagement with the septum after repeated percutaneous injections. Additionally, all-plastic ports are susceptible to nicks and scratches on the interior surface by the accessing needle. These nicks and scratches could lead to nidus, blood clots, or precipitation formations.

Efforts have been made to combine the advantages of all-metal ports with all-plastic ports. For example, in U.S. Pat. No. 4,802,885 to Weeks et al., a metal reservoir having a chamber sealed by a pre-formed silicone septum is jacketed by a single piece of a silicone elastomer. However, all-metal ports jacketed by a single piece of elastomer have significant shortcomings. These shortcomings include quality control problems during manufacturing, and expensive molding processes.

Other efforts have focused on providing a multiple piece all-plastic housing in cooperation with an open metal cup to sealingly engage a septum. For example, see U.S. Pat. No. 5,213,574 to Tucker. This design has shortcomings associated with it, including defects in the plastic housing which may cause an improperly sealed septum. Once the septum is improperly sealed the entire port must be discarded.

Therefore a need has arisen for an access port device which addresses the problems of prior port devices.

A variety of implantable devices, known as subcutaneous access ports, are utilized to deliver fluids to or to withdraw fluids from the bloodstream of a patient. Such access ports typically include a needle-impenetrable housing which encloses one or more fluid cavities and defines for each such fluid cavity an access aperture communicating through the housing on the side thereof which is adjacent to the skin of the patient when the access port is implanted in the body. A needle-penetrable septum is received in and seals each access aperture. Exit passageways located in an outlet stem communicate with each of the fluid cavities for dispensing medication therefrom to a predetermined location in the body of the patient through an implanted catheter attached to the access port.

Once the access port and the catheter have been implanted beneath the skin of a patient, quantities of medication or blood may be dispensed from one such fluid cavity by means of a non-coring needle passed through the skin of the patient and penetrating the septum into one of the respective fluid cavities. This medication is directed through the distal end of the catheter to an entry point into the venous system of the body of the patient.

Blood may also be withdrawn for sampling from the body of a patient through such an access port. This is accomplished by piercing the skin of the patient and one of the respective septums with a non-coring needle and applying negative pressure thereto. This causes blood to be drawn through the catheter into the fluid cavity corresponding to the pierced septum and then out of the body of the patient through the needle.

To prevent clotting thereafter, the withdrawal route is flushed with a saline solution or heparin using again a non-coring needle piercing the skin of the patient and the septum in the same manner as if a medication were being infused.

Both intermittent and continual injections of medication may be dispensed by the access port. Continual access involves the use of a non-coring needle attached to an ambulatory-type pump or a gravity feed IV bag suspended above the patient. The ambulatory-type pump or the IV bag continually feeds the medication or fluid through the needle to the fluid cavity in the access port and from there through the catheter to the entry point into the venous system.

To facilitate locating each respective septum once the access port has been implanted, some access ports incorporate a raised circular ring located about the outer perimeter of the septum. This raised ring enhances the tactile sensation afforded by the subcutaneous septum to the palpating fingertip of a medical practitioner. Alternatively, other access ports have utilized palpation ridges rather than a raised circular ring for substantially the same purpose. The palpation ridges allow the location of the septum to be accurately determined when the access port is subcutaneously implanted.

To preclude reaction with the tissues in the body of the patient, access ports are constructed of nonreactive materials, such as titanium or stainless steel. Although these materials are nonreactive, access ports constructed utilizing titanium or stainless steel materials produce an interfering or blurred image of the body of the patient in the vicinity of the implanted access port when diagnostic imaging techniques such as magnetic resonance imaging ("MRI"), CAT scans, or computerized tomography are used. The blurred region caused by the presence of a metallic access port in the body of a patient extends beyond the access port itself. Therefore, the use of metallic access ports limits the diagnostic imaging techniques that may be used relative to those areas of the body in which an access port is implanted. In place of metallic materials some access ports have been fabricated at least in part from biocompatible plastics.

A further problem relating to the materials for and manufacture of access ports is the deleterious impact of some manufacturing procedures on the fluids which flow through the fluid cavities and related structures located between the fluid cavities and the catheter. During the manufacture of an access port, whether the port is comprised of metallic or plastic materials, it becomes necessary to form the fluid cavities and exit passageways through which the fluid will be directed into the attached catheter. This manufacturing process often leaves sharp edges, seams and corners in the areas where the fluid cavity is to direct the flow of the fluid through an exit passageway. As blood or other fluids are injected through the septum into the fluid cavity, pressure developed within the fluid cavity tends to cause fluid to flow through the exit passageway. As the fluid in the fluid cavity flows past the sharp edges and corners produced in the manufacture of the access port, turbulence arises, taking the form of a vortex, adjacent to the sharp edges and corners. Some fluids, such as blood, are sensitive to this turbulence, and lysing of the red blood cell component of the injected blood can occur in these turbulent areas.

In addition, the production of the circular fluid cavities often results in the creation of areas within the housing in which fluid flow is retarded. These areas are referred to as dead spaces and usually occur in areas of transition, such as where the bottom of the septum interfaces with the walls of the fluid cavity and where the floor of the fluid cavity meets the exit passageway through which the fluid must flow. As the flow of fluids through dead spaces is retarded, stagnation occurs, resulting in some fluid being trapped within these dead spaces. If the access port is used to withdraw or transfuse blood, blood trapped in these dead spaces may form clots and block the flow of fluid through the fluid cavity.

Moreover, in some prior vascular access ports the internal reservoirs are formed by two plastic parts with are bonded together. This results in an undesirable seam being formed where the adjacent parts abut one another. The inside of the reservoir should be as smooth as possible to help prevent damage to blood cells or the initiation of blood clotting during infusion or withdrawal of blood through the port.

A further problem encountered in the design and construction of access port relates to the positioning of the septums within the housing of the access port. The positioning of the septums within the housing is a compromise between two conflicting objectives. These are the need to separate the septums to such a distance so that the septums may be easily differentiated for the purpose of injection and the need to restrict the overall dimensions of the access port for patient comfort and aesthetics. The distancing of the septums to facilitate their differentiation, however, results in a corresponding distancing of the fluid cavities. This result is at odds with another structural requirement for access ports with plural cavities, namely that the exit passageways from each fluid cavity be closely spaced at the point where the implanted catheter is to be coupled to the access port.

To guide the flow of a fluid from each of the spatially separated fluid cavities into the side-by-side configuration of fluid outflow necessitated by the dimensions of a plural lumen catheter, intermediate structural members have been required. Naturally, this complicates the process of manufacture and increases its cost, as well as the changes of structural failure.

There are several examples of such intermediate members used to resolve the manufacturing constraints imposed upon the construction of a passageway flowing from spatially separate fluid cavities into a side-by-side configuration acceptable by a catheter. One is to produce passageways in the form of bent metal tubes which are then insert molded or welded into the larger body of the access port. The use of such a metal component will interfere with the production of an access port which is free of limits as to the diagnostic imaging techniques that may be used relative to those areas of the body in which an access port is implanted. In addition, the integral nature of such metal outlet passageways raises the possibility of leakage of medication through the interstices between the metal tubes and the body of the access port.

Alternatively, to produce fluid flow from spatially separated fluid cavities into the closely spaced lumens of a catheter, each fluid cavity has been designated with its own spatially separated outlet stem. These outlet stems are then coupled by a hub structure for permanent attachment to the closely spaced lumens of a catheter. This type of arrangement increases the size of the overall access port and its cost of manufacture by adding thereto the necessity of fabricating and assembling of the hub element. Port connections to catheters in this manner are permanent. Accordingly, if the catheter is to be shortened by trimming, that trimming must occur at the distal end of the catheter, and this precludes the use of any type of specially designed tip or valve.

An additional set of problems encountered in the use of access ports relates to the actual connection of the catheter to the access port. This is most commonly effected by securing the catheter to an outlet stem protruding from the housing of the access port. In an attempt to lock the catheter to the outlet stem of the access port, thread-type systems have been developed wherein the catheter is attached to an outlet stem, and the outlet stem is then threaded into the access port. When utilizing this system, however, it is difficult to determine the amount of engagement of the catheter onto the outlet stem. Some catheter connection systems do not allow visual verification of attachment. As a result, leakage and failure can occur.

To overcome this problem, access ports are produced in which the catheter is pre-attached at the factory. While this practice alleviates many of the problems with leakage and failure due to catheter slippage, this system severely limits the type of the catheter usable with the access port. This precludes the use of catheters having specialized distal tips, as the distal end of the catheter is the only end that can then be trimmed to effect its ultimate sizing. For example, catheters utilizing a Groshong® slit valve at their distal end may not have any of the distal tip of the catheter removed without compromising the catheter.

Thus, there has been a need for an improved vascular access port which overcomes the above-noted problems, and which can be manufactured economically. The present invention fulfills these needs and provides other related advantages.

SUMMARY

One aspect of the instant disclosure relates to access port for providing subcutaneous access to a patient. More particularly, an access port may comprise a body configured for capturing a septum for repeatedly inserting a needle therethrough into a cavity defined within the body. Further, the septum may include at least one topographical feature configured for identification of the septum. Also, a septum for an access port for providing subcutaneous access to a patient is encompassed by the instant disclosure, wherein the septum may comprise a body exhibiting at least one topographical feature configured for identification of the septum.

A further aspect of the instant disclosure relates to an access port for providing subcutaneous access to a patient including a body configured for capturing a septum for repeatedly inserting a needle therethrough into a cavity defined within the body, and a means for identification of the septum. In one embodiment, the means for identification may comprise at least one topographical feature of a surface of the septum. In another embodiment, means for identification may comprise a visually perceivable feature selected from the group consisting of: a color, a symbol, a letter, a pattern, and indicia. In a further embodiment, means for identification may comprise an x-ray detectable feature or an ultrasound detectable feature. In yet an additional embodiment, means for identification may comprise an RFID tag.

Another aspect of the instant disclosure relates to a method of identifying a subcutaneously implanted access port. More particularly, an access port including a septum may be provided. Further, at least one topographical feature of the septum of the access port may be perceived. In addition, the subcutaneously implanted access port may be identified in response to perceiving the at least one feature of the septum of the access port.

Features from any of the above mentioned embodiments may be used in combination with one another in accordance with the instant disclosure. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Advantages of the instant disclosure will become apparent upon review of the following detailed description and drawings, which illustrate representations (not necessarily drawn to scale) of various aspects of the instant disclosure, wherein:

FIGS. 2A-2E depict various views of the preferred single-port implantable access device of the present invention;

FIG. 3A-3D depict various views of another embodiment of the implantable access device of the present invention;

DETAILED DESCRIPTION

Figure 1B:
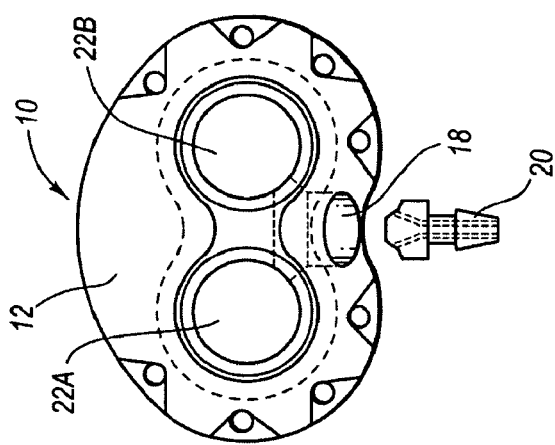
FIGS. 1A-1D depict various views of the preferred dual-port implantable access device of the present invention.
Figure 1D:
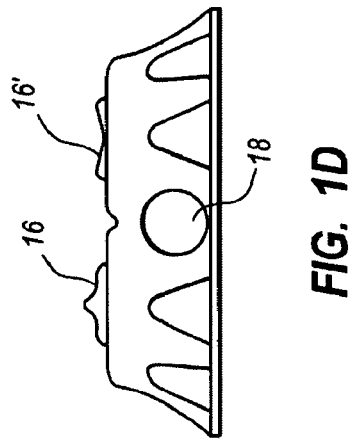
Figure 1A:
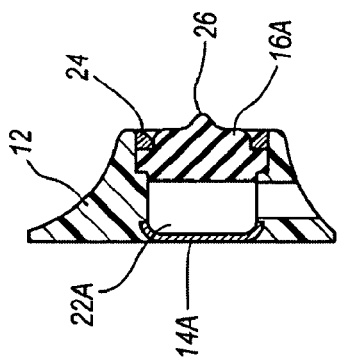
Figure 1C:
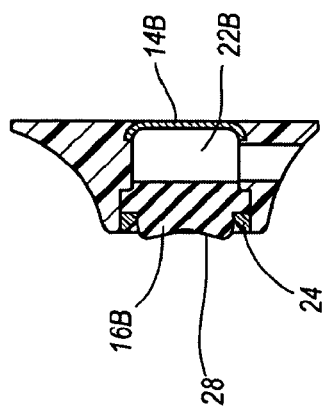

FIGS. 1A-1D depict various views of the preferred dual-port implantable access device 10 of the present invention. The port 10 generally comprises a housing member 12 defining fluid chambers 22A and 22B. The chambers are sealed by the housing 12, bottom cup members 14A and 14B, and self-sealing septum members 16A and 16B. In this embodiment, the housing 12 is preferably formed of titanium, stainless steel, ceramic, and/or other biocompatible material. The septum 16A and 16B is preferably formed of silicon or other semi-permeable materials that permit ingress and egress of needles to deliver fluid to the chambers 22A and/or 22B. An exit port 18 is provided in communication with chambers 22A and 22B, which delivers fluid out of the chambers 22A and/or 22B to a predetermined location, via stem 20 and attached catheter (not shown), as is understood in the art.

The septums 16 are formed with a generally circular shape, and, as shown in the drawings, may include a nipple 26 or a concave portion 28 on the outer surface thereof. The nipple is advantageous for visual and/or tactile location of the port device 10, and as a locator for needle insertion. Likewise, concave portion 28 provides similar features, but may be used in areas where a protruding nipple is undesirable. The septums 16A and 16B and housing 12 are preferably formed with mated tongue and groove portions, as shown in the side view drawings of FIGS. 1A and 1C. The housing may further include molded top member 24 which press against the septum for further stability.

As opposed to plastic materials used in the prior art, the cup portion 14 is preferably formed of titanium or stainless steel to resist scratches and/or debris from being introduced into the chambers, as a result of needle impacts thereon. Preferably, cup 14A and 14B is attached to housing 12 via insert molding, interference fit, ultrasonic weld, biocompatible glue, and/or other attachment means. FIGS. 2A-2E depict a single-port version of the port device of the present invention, and is similarly constructed as shown in FIGS. 1A-1D.

FIG. 3A-3D depict another embodiment of the port device of the present invention. In this embodiment, the cup member 14' includes sidewall portions 28 that are dimensioned to fit within the chamber 22', defined by housing 12'. The cup member 14' is attached to the housing 12' by insert molding, interference fit, ultrasonic weld, biocompatible glue, or other attachment means known in the art. The septum 16' is similar to the septum 16A and/or 16B and may also include a nipple or concave portion, described above. In this embodiment, a metal ring 30 is provided which circumscribes the top of the housing 12' and is positioned above the septum 16'. The ring 30 preferably includes flange members 32, which have an upper surface dimensioned so as to urge a needle downward toward the septum, thus preventing errant entry of needles within the septum. In this embodiment the ring structure is formed of titanium, stainless steel or ceramic material for increase mechanical resistance to puncture and/or tear. Accordingly, since the ring member 30 will protect the other components, the housing can be formed of less expensive material, e.g., plastics, etc. The ring member 30 and housing 12' preferably include mated tongue and groove portions to hold the ring member securely against the housing, as shown. Additionally, the lower surface of the flange members 32 are dimensioned so as to force against the septum, thereby holding the septum in place.

Figure 4:
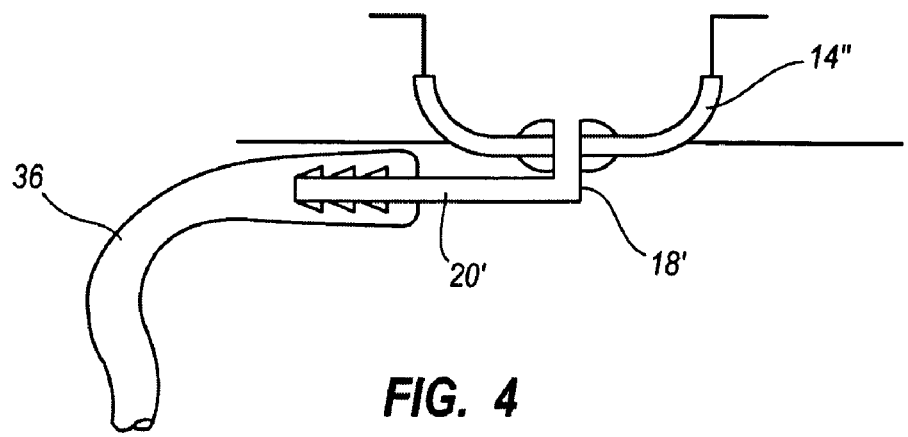
FIG. 4 depicts an alternative embodiment of the cup member of FIGS. 1-3.
Figure 5A:
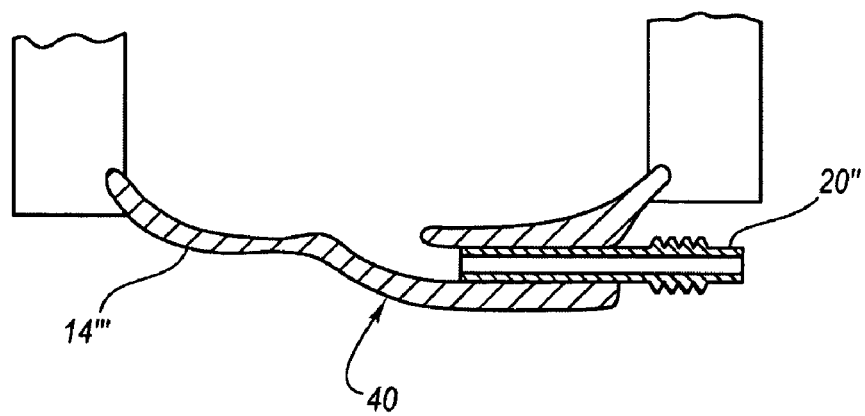
FIGS. 5A and 5B depict views of another alternative embodiment of the cup member of FIGS. 1-3.
Figure 5B:
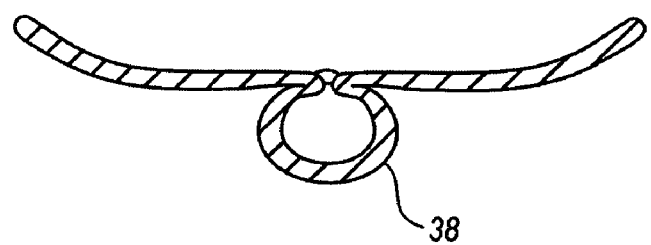

FIGS. 4 and 5A-5B depict alternative embodiments for the cup member described above in FIGS. 1-3. In the embodiment of FIG. 4, the cup member 14" defines an exit port 18' therein, and preferably located at the bottom portion of the cup 14", as shown. A stem 20' is connected to the port 18' at one end, and a catheter 36 is connected to the other end of the stem 20'. So as to provide a low-profile shape, it is preferred that the stem 20' includes an elbow, or angled portion, to direct fluid sideways away from the port, as shown. In FIGS. 5A and 5B, the cup 14''' is formed with a flange 40 to define an opening 38 that is dimensioned to accept a stem 20" therein. The cup 14" and/or 14''' are provided to better anatomically fit into the subcutaneous areas around muscle tissue, and each are connected to the housing (not shown) in a manner similar to the embodiments of FIG. 1, 2 or 3.

Figure 6:
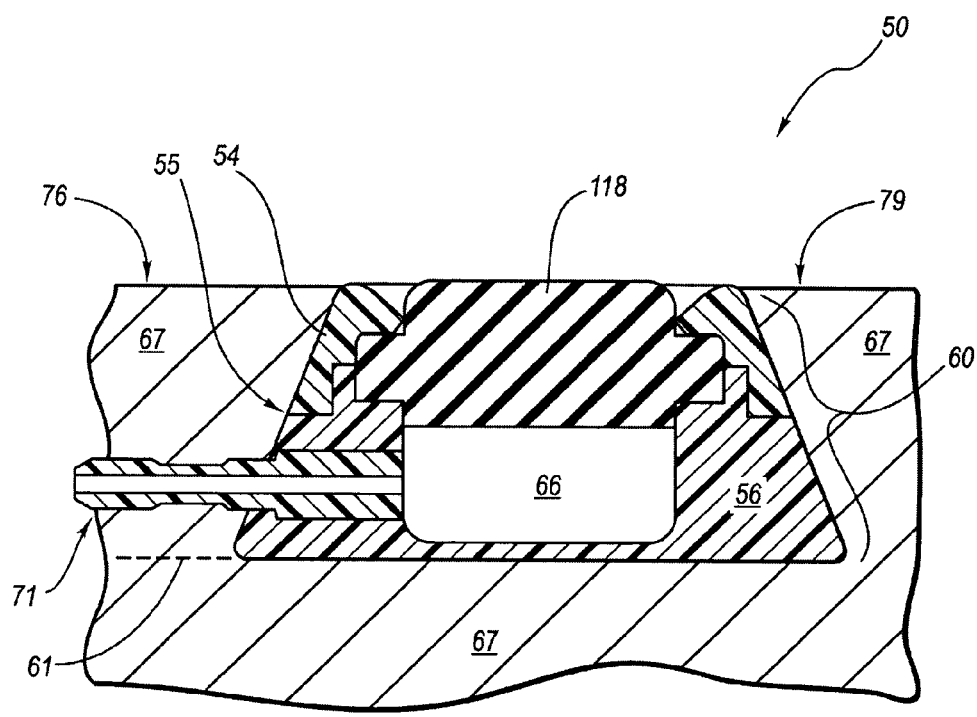
FIG. 6 shows a schematic, side cross-sectional view of a subcutaneously implanted access port.

As discussed above, access ports may provide percutaneous access to a patient. In further detail, referring to FIG. 6 shows a schematic, side cross-sectional view of another embodiment of an access port 50, which is implanted within a patient. In further detail, access port 50 includes a housing or body 60 defined by a cap 54 and a base 56. Cap 54 and base 56, as known in the art, may be configured for capturing therebetween a septum 118. As shown in FIG. 6, cap 54 and base 56 may matingly engage one another along a mating line 55. Cap 54 and base 56 may be secured or affixed to one another via mechanical fasteners such as screws or other fastening devices, may be adhesively affixed to one another, or may be affixed to one another as known in the art. Further, cap 54, base 56, and septum 118 may collectively define a cavity 66 in fluid communication with a lumen of outlet stem 71. As shown in FIG. 6, the body 60 of access port 50 may be implanted in a patient 67 to position the cavity 66 subcutaneously within the patient 67. As known in the art, sutures (may be used to affix the access port 50 within the patient 67, if desired. After the body 60 is implanted in a patient 67, the upper surface of the septum 118 may be generally flush or aligned with the surface of the skin surface 76 of the patient 67 and may be repeatedly punctured for creating a percutaneous passageway from the exterior of the skin of the patient into the cavity 66. The outlet stem 71 may create a fluid-communicative passageway from the cavity 66 through the outlet stem 71 and into the interior of the patient 67. As mentioned above, a catheter may be coupled to the outlet stem 71 for fluid communication with the cavity 66 and for transferring fluid to a desired remote location from the cavity 66 and within a patient 67. Body 60 of access port 50 may comprise a biocompatible material such as polysulfone, titanium, or any other suitably biocompatible material as known in the art. Thus, generally, the body 60 may be formed from a biocompatible plastic material. Body 60 may include a concave bottom or, in another embodiment, may include a flat bottom, without limitation. Also, as mentioned above, access port 50 may comprise a so-called single port or a multiple port (e.g., dual port, triple port, etc.) configuration, without limitation.

One aspect of the instant disclosure contemplates that a septum of an access port may include at least one perceivable or identifiable feature for identifying the septum and, optionally, the access port. Of course, the identifiable feature may be perceivable after the access port is implanted within a patient. For example, at least one or perhaps multiple identifiable feature(s) of a septum of an access port may be correlative to information (e.g., a manufacturer's model or design) pertaining to the access port. Thus, an identifiable feature from an access port of a particular model may be unique in relation to most, if not all, other identifiable features of another access port of a different model or design. Of course, the at least one identifiable feature of an access port may be further correlative with any information of interest, such as type of port (e.g., power-injectable port), catheter type, date of manufacture, material lots, part numbers, etc. In this way, once at least one identifiable feature of an access port is observed or otherwise determined, correlation of such at least one feature of an access port may be accomplished, and information pertaining to the access port may be obtained. Accordingly, "identification," as used herein and in connection with a septum, means to provide the ability to correlate selected information of interest with a perceivable feature of a septum.

In one embodiment, at least one feature may be perceived by palpation (i.e., to examine by touch), by way of other physical interaction, or by visual observation. Accordingly, a person may touch or feel the septum of the access port to perceive at least one identifying characteristic of the septum. In another embodiment, at least one identifiable feature may be perceived via x-ray or ultrasound imaging. In yet a further embodiment, at least one identifiable feature may be perceived through magnetic, light, or radio energy interaction or communication with the septum.

Figure 7:
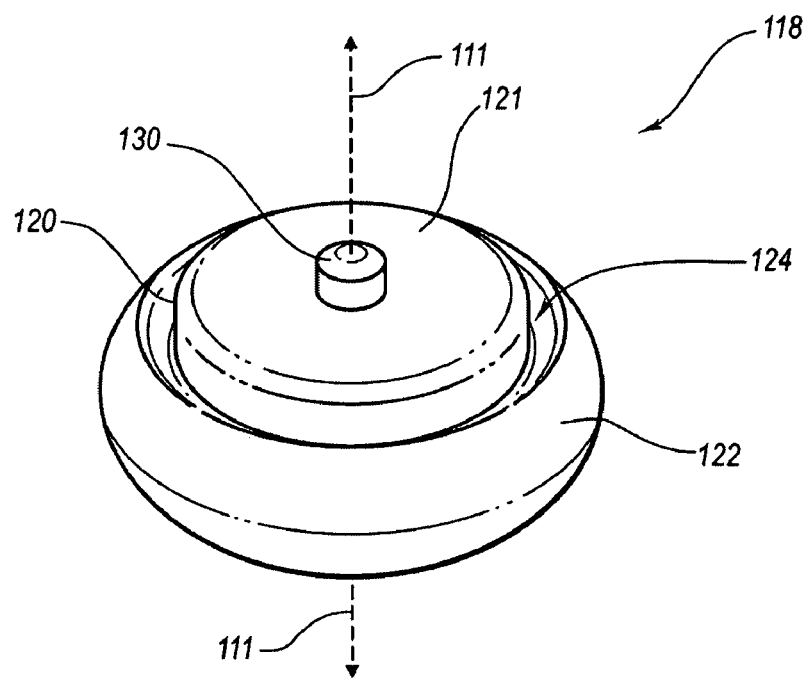
FIGS. 7 and 8 show a perspective view and a schematic side view, respectively, of a septum including a protrusion.
Figure 8:
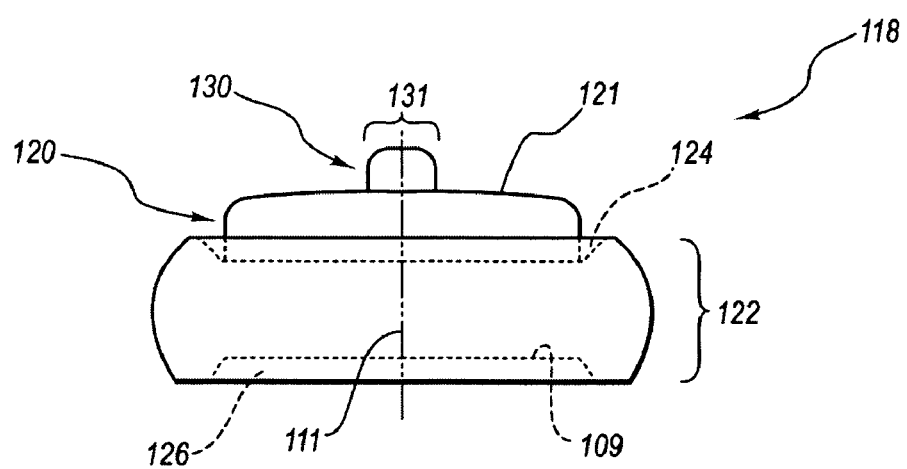

Turning to the embodiment wherein at least one feature may be perceived through palpation, other physical interaction, or visual observation, a topography or exterior surface feature of a septum of an access port may be configured for perception. For example, the instant disclosure contemplates that a septum may include at least one topographical feature configured for identifying the access port after it is implanted. More particularly, FIGS. 7 and 8 show a perspective view and a schematic side view, respectively, of a septum 118 including at least one topographical feature. Generally, septum 118 may include a base region 122 and an elevated region 120 extending from the base region 122 and including a septum surface 121. As noted in the art, septum 118 may be structured for assembly within the housing, wherein the housing causes at least a portion of the septum 118 to be compressed. Such compression may facilitate sealing of a puncture or aperture, which is, formed between septum surface 121 and septum surface 109. FIGS. 7 and 8 show one embodiment of septum 118, which includes an annular recess 124 extending circumferentially about raised region 120 as well as a recess 126 that is formed into base region 122. Further, as shown in FIGS. 7 and 8, septum 118 may be substantially symmetric about central access 111. Such a configuration may facilitate substantially uniform compression within at least a portion of base region 122 when a periphery of base region 122 is compressed. Additionally, a protrusion 130 may extend from septum surface 121 and may be configured for identifying septum 118 (and, optionally, an access port with which septum 118 is assembled). Accordingly, protrusion 130 may have a selected size and shape that allows for perception through palpation. As shown in FIGS. 7 and 8, protrusion 130 may, optionally, include a generally rounded end 131. Such a configuration may provide a protrusion structured for identification of septum 118, which is relatively robust and resists damage in response to repeated physical interactions, such as, palpation. Of course, protrusion 130 may exhibit various selected characteristics, such as, for example, fillets, chamfers, concave surfaces, convex surfaces, through-holes, cavities, grooves, or other geometric features as may be desired.

Figure 9:
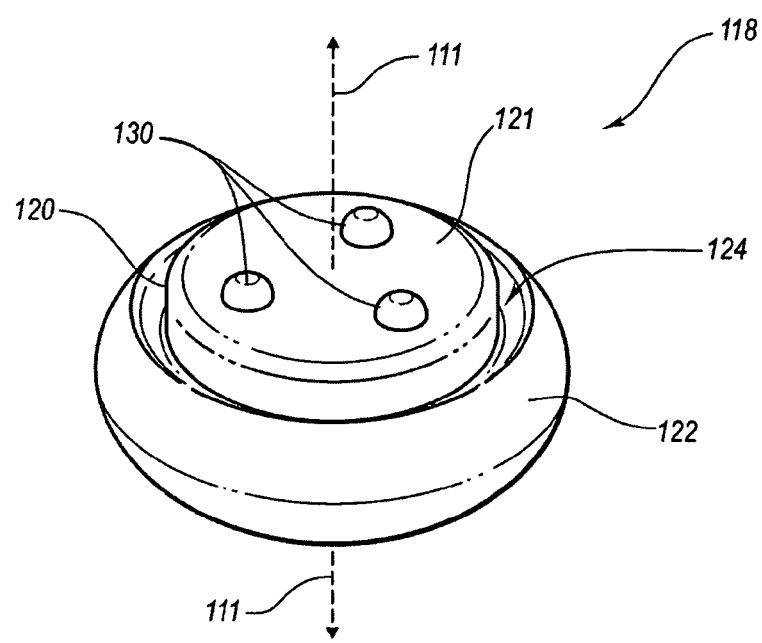
FIGS. 9 and 10 show a perspective view and a schematic side view, respectively, of a septum including a plurality of protrusions.
Figure 10:
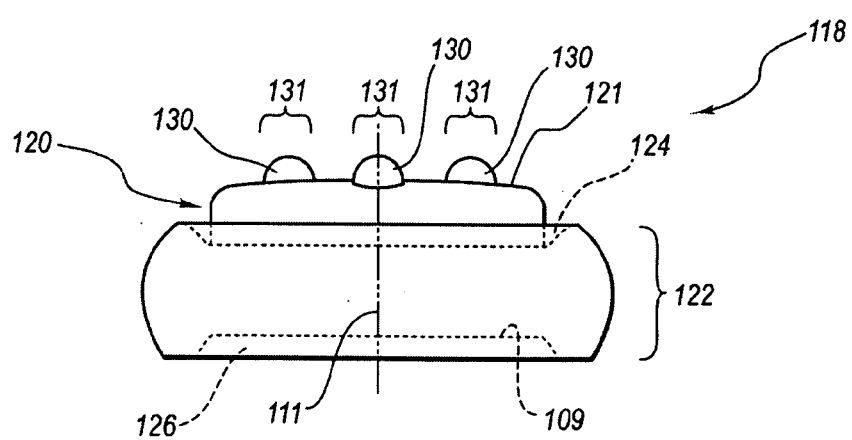
Figure 11:
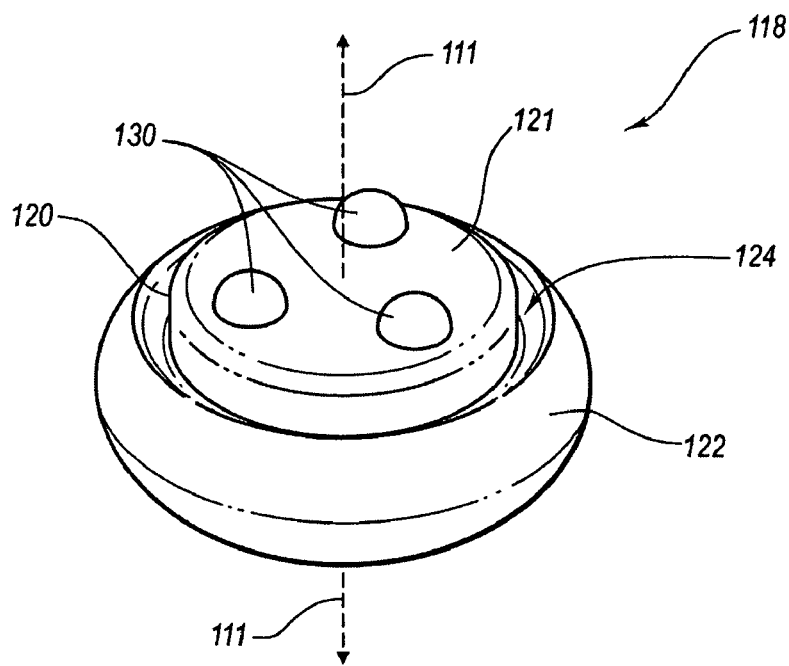
FIGS. 11 and 12 show a perspective view and a schematic side view, respectively, of another embodiment of a septum including a plurality of protrusions.
Figure 12:
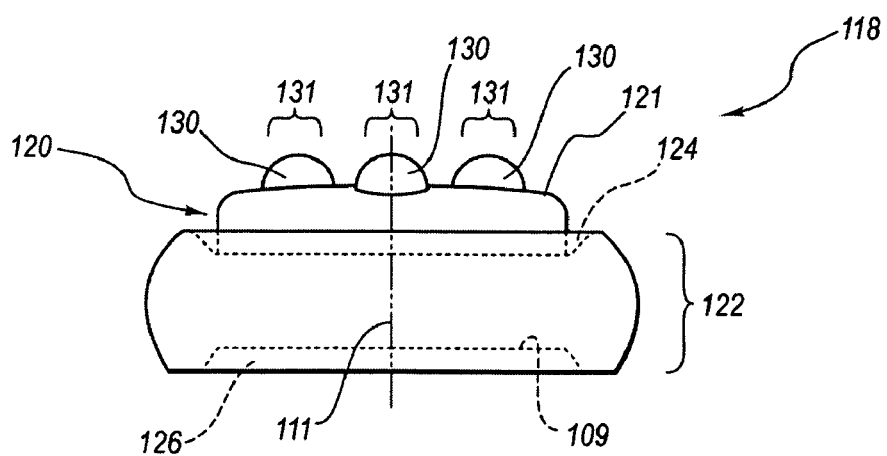

The instant disclosure further contemplates that a septum may include a plurality of protrusions that, collectively, are structured for perception and identification of the septum. For example, FIGS. 9 and 10 show a perspective view and a schematic side view, respectively, of a septum 118 including three protrusions 130. Septum 118, as shown in FIGS. 9 and 10, may be generally configured as described above with respect to FIGS. 6 and 7. However, as shown in FIGS. 9 and 10, septum 118 may include protrusions 130, which are substantially identical. Further, optionally, protrusions 130 may be positioned substantially equidistantly from central access 111, as shown in FIGS. 9 and 10. Such a configuration may allow for perception of protrusion 130, identification of the septum 118 in response to perception of protrusions 130, and may also allow for an indication of the position of central access 111 (i.e., a center of septum surface 121). As shown in FIGS. 9 and 10, each of protrusions 130 may include a generally rounded end 131. In other embodiments, each of protrusions 130 may have an end that is configured as desired (e.g., similarly, substantially identically, or differently), without limitation. Moreover, it may be appreciated that protrusions 130 may embody various selected positions, sizes, or configurations upon a septum for perception and identification of such a septum. For example, FIGS. 11 and 12 show a perspective view and a schematic side view, respectively, of another embodiment of a septum 118 including three protrusions 130 that are larger than the protrusions 130 shown in FIGS. 9 and 10. As shown in FIGS. 11 and 12, protrusions 130 may be substantially equidistantly positioned about central access 111 and each of protrusions 130 may include a generally rounded end 131 (e.g., at least partially spherical, generally convex, or generally ovate).

Figure 13:
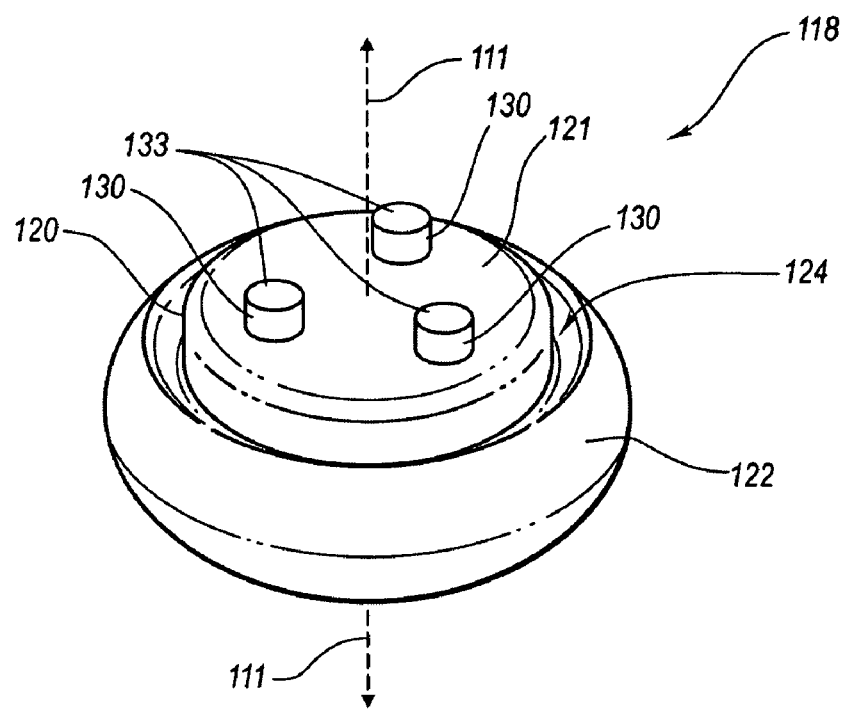
FIGS. 13 and 14 show a perspective view and a schematic side view, respectively, of a further embodiment of a septum including a plurality of protrusions.
Figure 14:
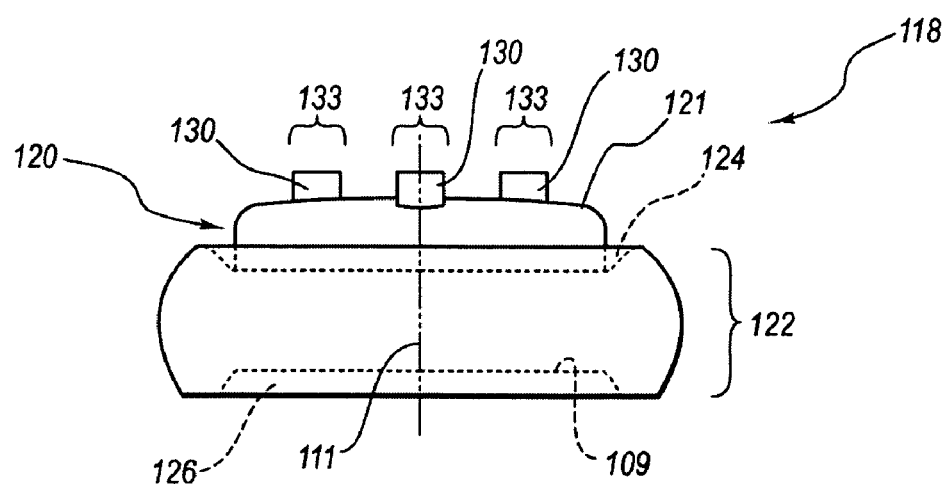
Figure 15:
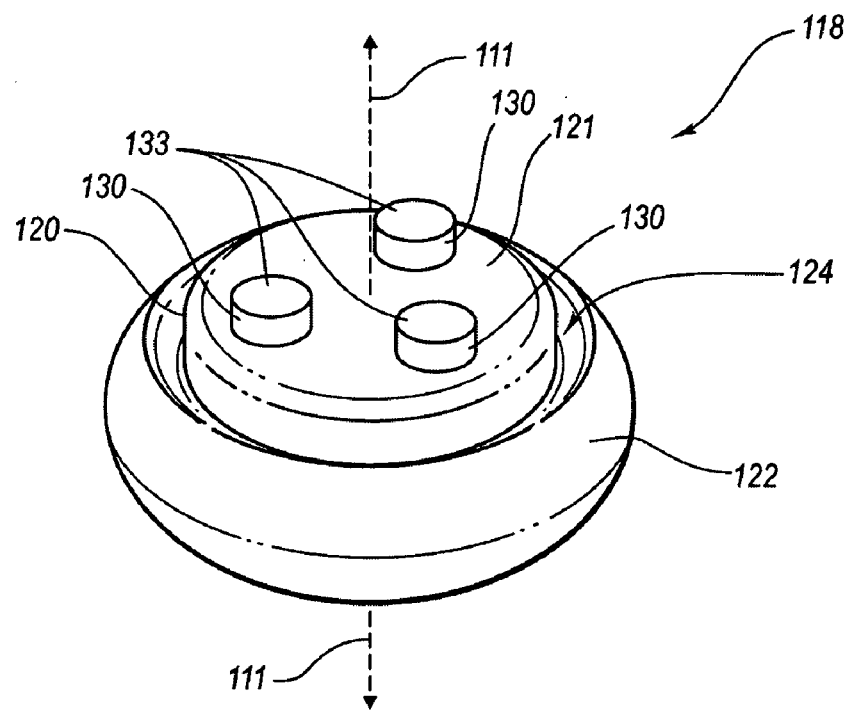
FIGS. 15 and 16 show a perspective view and a schematic side view, respectively, of yet an additional embodiment of a septum including a plurality of protrusions.
Figure 16:
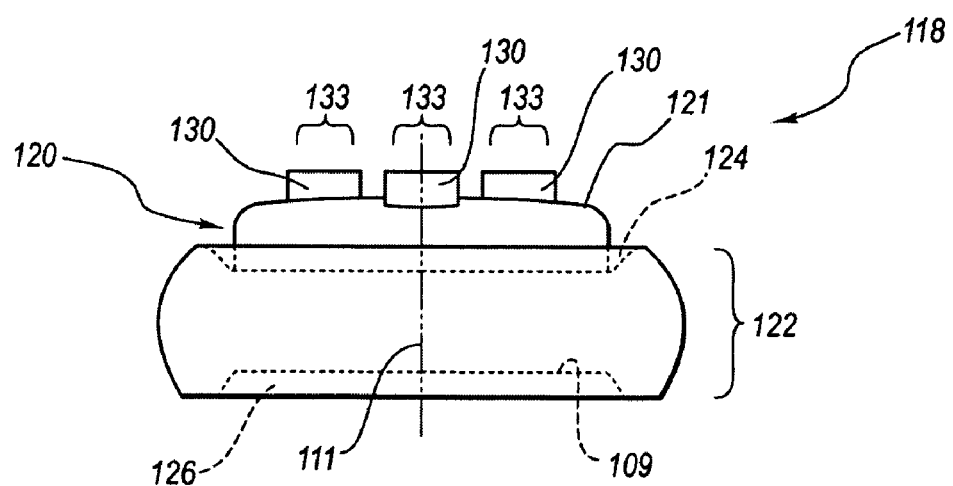

As mentioned above, the instant disclosure contemplates that a septum may include at least one protrusion and that the protrusion may be configured, as desired, for perception and identification of the septum. For example, a protrusion extending from a surface of a septum may include at least one substantially planar surface. FIGS. 13 and 14 show a perspective view and a schematic side view, respectfully, of a septum 118 including protrusions 130, each of which includes a substantially planar surface or substantially planar end 133. Otherwise, septum 118, as shown in FIGS. 13 and 14, may be configured generally as described above with respect to FIGS. 9 and 10. As shown in FIGS. 13 and 14, protrusions 130 may be generally cylindrically as they extend from septum surface 121. Of course, in other embodiments, protrusions 130 may taper as they extend from septum surface 121. In addition, the cross-sectional shape of protrusions 130 (taken transverse to the direction of extension from septum surface 121) may be generally circular, generally rectangular, generally triangular, generally oval, or generally polygonal, without limitation. Of course, the size of each of protrusions 130 may be selected for providing an identifiable topography to septum 118. For example, in another embodiment, FIGS. 15 and 16 show a perspective view and a schematic side view, respectively, of a septum 118, which is generally configured as described above with reference to FIGS. 13 and 14, but includes protrusions 130 that are larger than the protrusions 130 as shown in FIGS. 13 and 14. Such a configuration may be perceivably different (e.g., by palpation) from the embodiment of septum 118 as shown in FIGS. 13 and 14.

Figure 17:
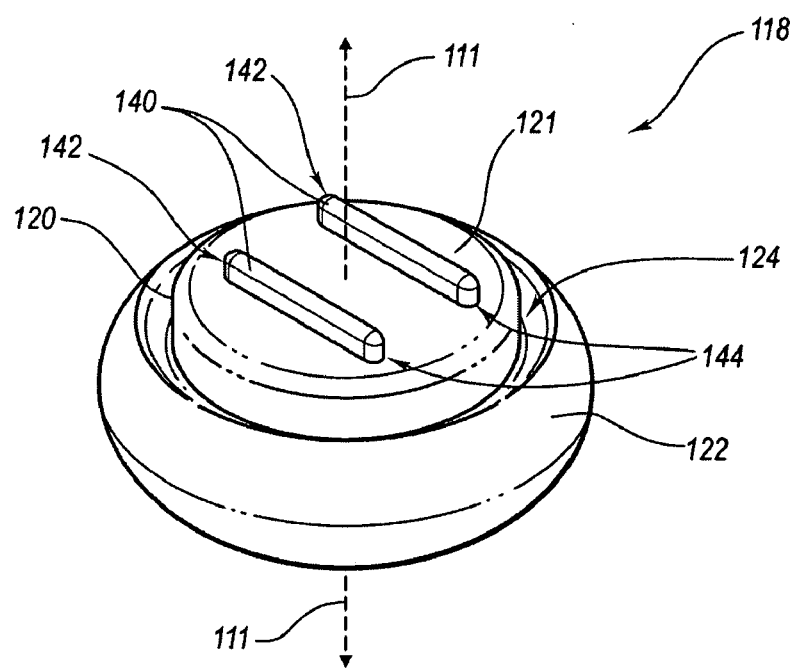
FIGS. 17 and 18 show a perspective view and a schematic side view, respectively, of a septum including a plurality of elongated protrusions.
Figure 18:
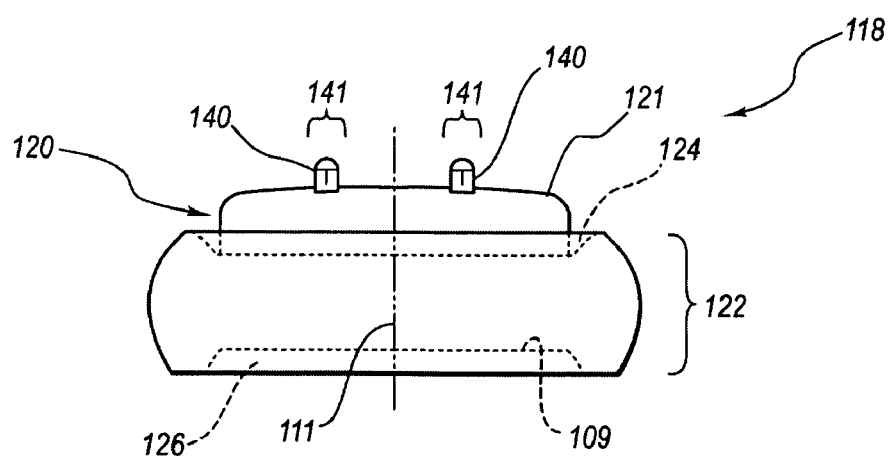
Figure 19:
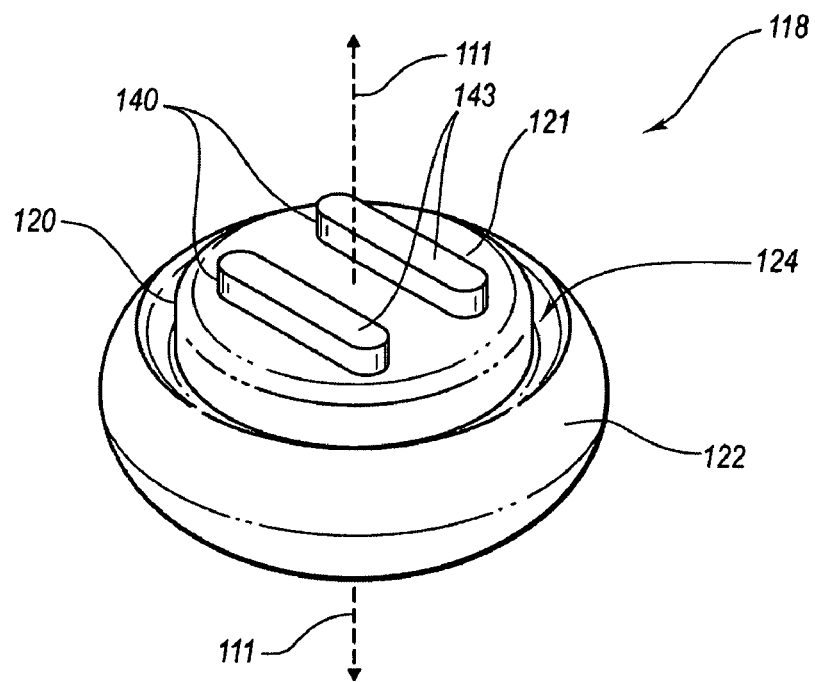
FIGS. 19 and 20 show a perspective view and a schematic side view, respectively, of another embodiment of a septum including a plurality of elongated protrusions.
Figure 20:
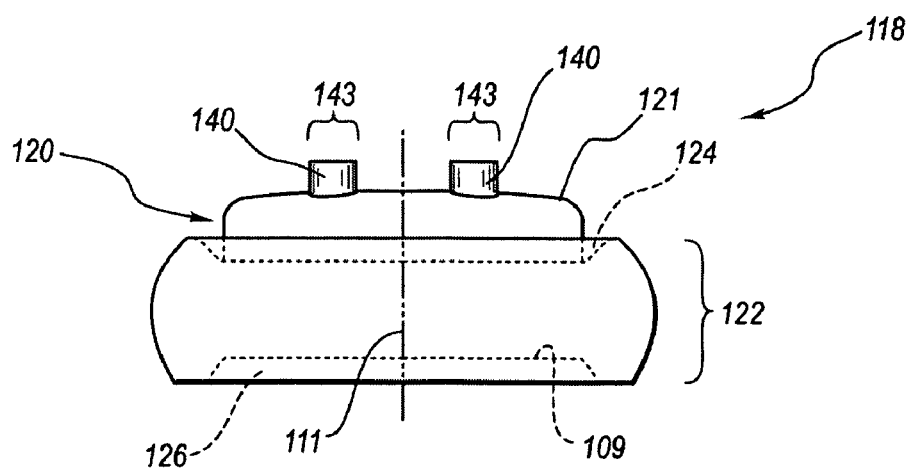

As mentioned above, at least protrusion of a septum may be sized, shaped, and structured as desired. For example, in another embodiment, a septum may include at least one protrusion that is elongated. For example, FIGS. 17 and 18 show a perspective view and a schematic side view, respectively, of a septum 118 including elongated protrusions 140. As shown in FIGS. 17 and 18, elongated protrusions 140 may each extend between a lateral end 142 and a lateral end 144, generally along a linear (i.e., straight) path. Of course, in other embodiments, elongated protrusions 140 may extend along respective arcuate paths between each of lateral ends 142 and 144, respectively. Furthermore, at least one elongated protrusion may form a pattern (e.g., spiral, substantially concentric rings, substantially parallel lines, intersecting lines, etc.). As shown in FIGS. 17 and 18, elongated protrusions 140 may extend up on septum surface 121 along substantially parallel paths. Further, elongated protrusions 140 may be substantially equidistantly positioned with respect to central access 111. As shown in FIGS. 17 and 18, each of the elongated protrusions 140 may exhibit a generally rounded boundary surface 141, as shown in FIG. 18. Of course, the instant disclosure contemplates that at least one elongated protrusion may embody various sizes, shapes, and configurations. For example, FIGS. 19 and 20 show a perspective view and a schematic side view of a septum 118 including elongated protrusions 140, each of which includes a substantially planar surface or substantially planar end 143. Thus, it may be appreciated that such a septum 118 may be perceivably distinguished from the septum 118 as shown in FIGS. 17 and 18.

Figure 21:
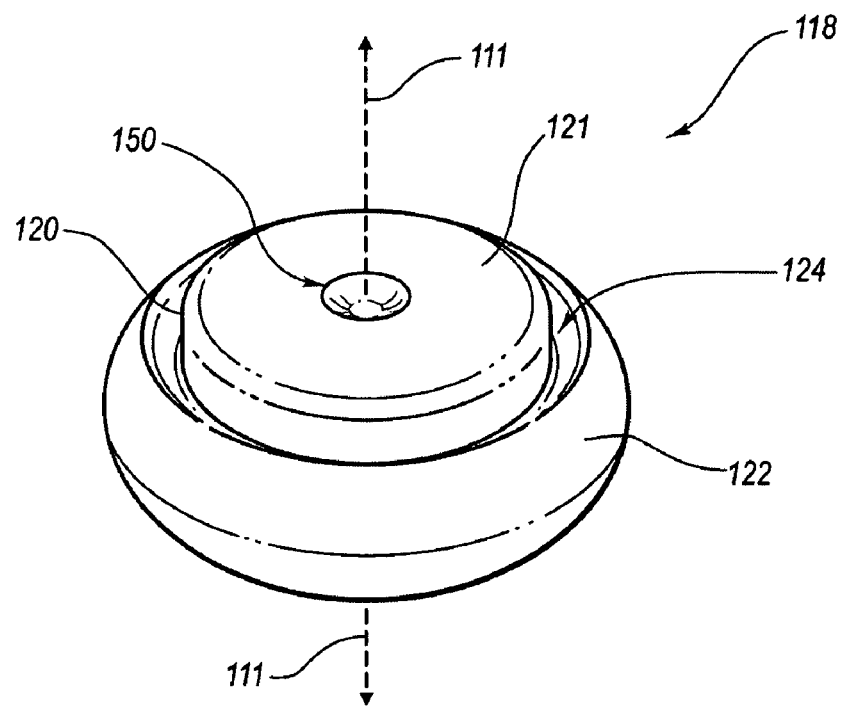
FIGS. 21 and 22 show a perspective view and a schematic side view, respectively, of a septum including a recess.
Figure 22:
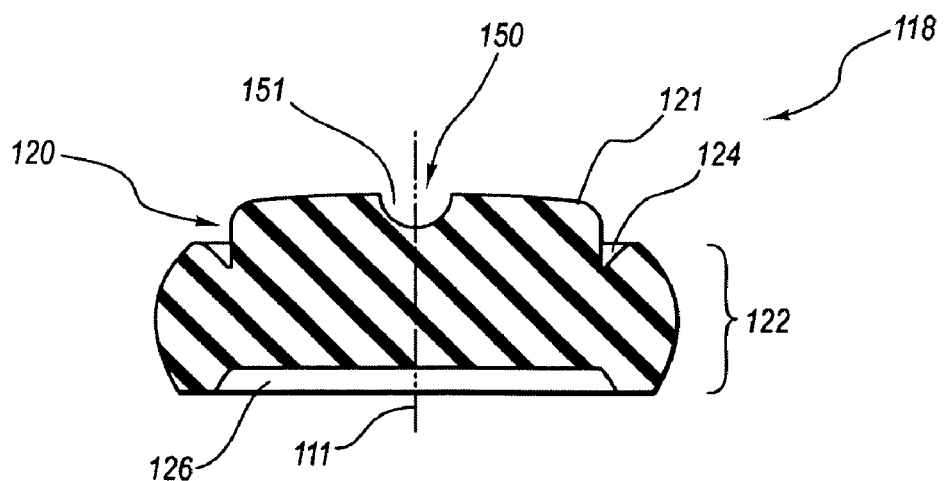

In a further aspect of the instant disclosure, a septum may include at least one recess that is structured for perception and identification of the septum. For example, FIGS. 21 and 22 show a perspective view and a schematic side cross-sectional view (taken through recess 150), respectively, of a septum 118 including a recess 150. As shown in FIGS. 21 and 22, recess 150 is defined by an arcuate surface 151, which is formed into septum surface 121. Also, recess 150 may be generally aligned with central access 111, if desired. Such a configuration may provide a perceivable feature for identifying septum 118. Of course, surface 151 may comprise a plurality of substantially planar surfaces or at least one arcuate surface (e.g., partially spherical, partially cylindrical, generally ovate, or any other arcuate surface known in the art). In addition, a periphery of recess 150 may be generally circular, as shown in FIGS. 21 and 22, or it may exhibit another selected shape. For example, without limitation, a periphery of a recess formed into a septum may be substantially oval, substantially rectangular, generally polygonal, star-shaped, or as otherwise may be desired.

Figure 23:
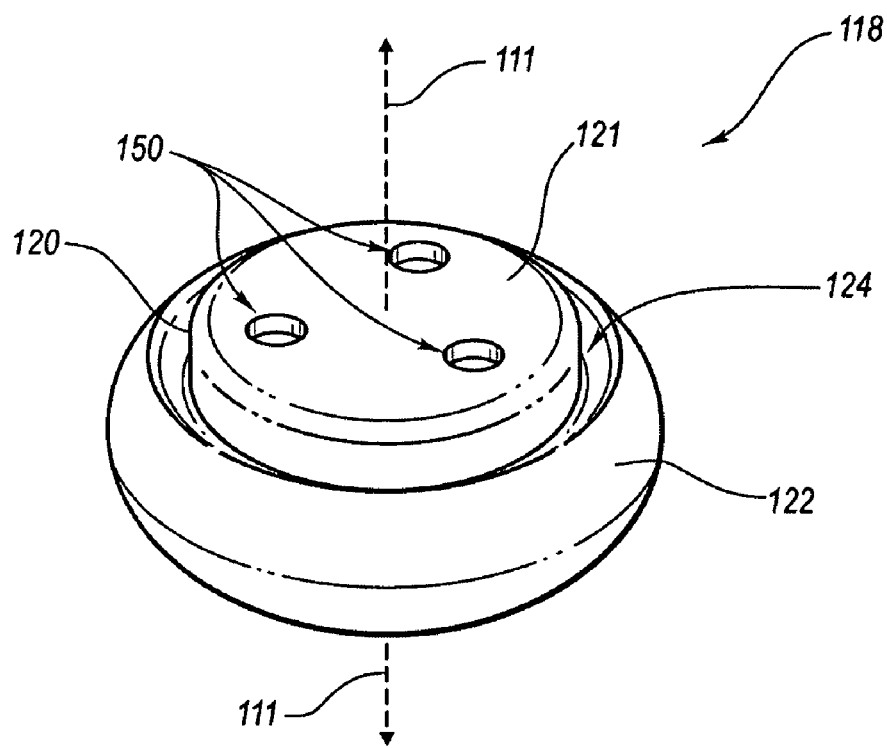
FIGS. 23 and 24 show a perspective view and a schematic side cross-sectional view, respectively, of a septum including a plurality of recesses.
Figure 24:
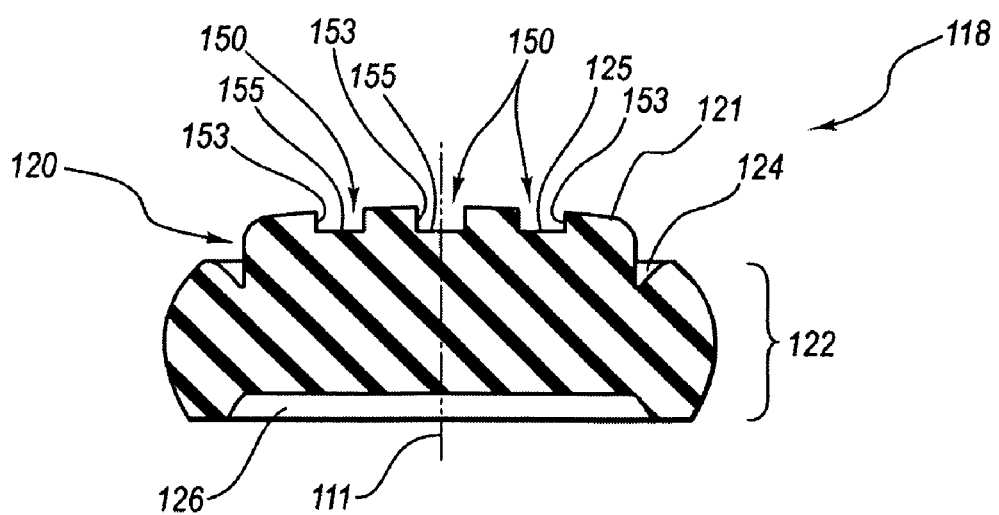

In another embodiment, a septum may include a plurality of recesses configured for perception (e.g., visual or by palpation) and identification of the septum. For example, FIGS. 23 and 24 show a perspective view and a schematic side cross-sectional view (taken through each of recesses 150) of a septum 118 including recesses 150. As shown in FIGS. 23 and 24, each of recesses 150 may be defined by an arcuate side surface 153 and a substantially planar interior surface 155. Further, each of recesses 150 may be positioned substantially equidistantly from central access 111 and may also be substantially equally circumferentially spaces from one another. Each of recesses 150 may have a selected depth into septum surface 121. For example, as shown in FIGS. 23 and 24, each of recesses 140 may exhibit a substantially equal depth. In other embodiments, at least one of recesses 150 may exhibit a depth that is different from at least another of recesses 150. In a further embodiment, each of recesses 150 may exhibit a different depth. Similarly, as shown in FIGS. 23 and 24, each of recesses 150 may be substantially identical. In other embodiments, one or more of recesses 150 may be configured differently than at least another of recesses 150.

Figure 25:
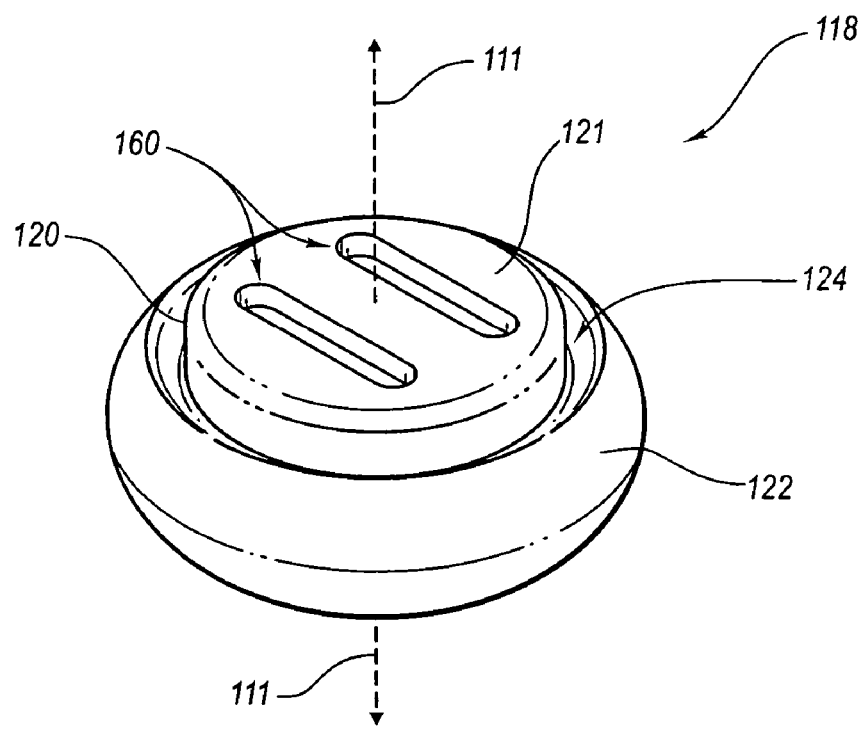
FIGS. 25 and 26 show a perspective view and a schematic side cross-sectional view, respectively, of a septum including a plurality of elongated recesses.
Figure 26:
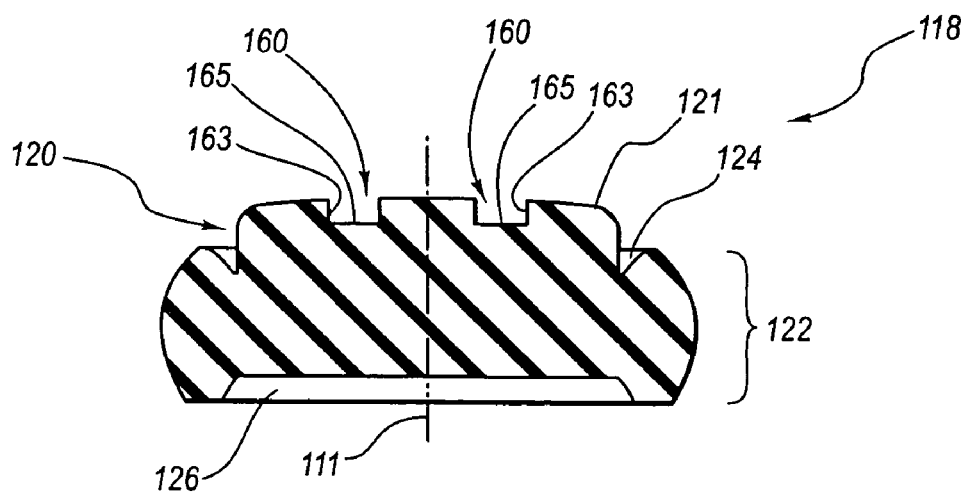

The instant disclosure also contemplates that at least one recess formed in a septum may comprise of at least one elongated recess. Thus, the instant disclosure contemplates that a septum may include at least one elongated recess configured for identifying the septum, an access part in which the septum is assembled, or both. For example, FIGS. 25 and 26 show a perspective view and a schematic side cross-sectional view (taken through elongated recesses 160), respectively, of a septum 118 including elongated recesses 160. Generally, each of elongated recesses 160 may extend along septum surface 121 along a selected path. For example, as shown in FIGS. 25 and 26, each of elongated recesses 160 may extend along a substantially linear or straight path. Optionally, as shown in FIGS. 25 and 26, the paths along which each of elongated recesses 160 follows may be substantially parallel to one another. Of course, in other embodiments, elongated recesses may be arcuate, non-parallel, or may at least partially intersect with one another. As shown in FIGS. 25 and 26, elongated recesses 160 may be positioned substantially equidistantly from central access 111. As discussed above in relation to elongated protrusions, at least one elongated recess may form a selected pattern. Such a pattern may be desirable for identifying a particular septum.

Figure 27:
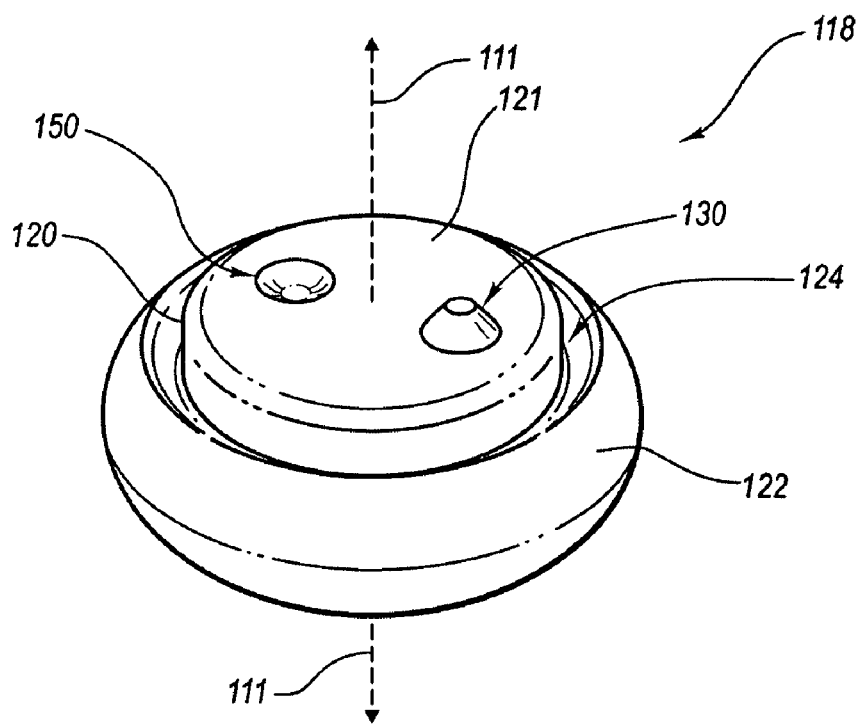
FIGS. 27 and 28 show a perspective view and a schematic side cross-sectional view, respectively, of a septum including a recess and a protrusion.
Figure 28:
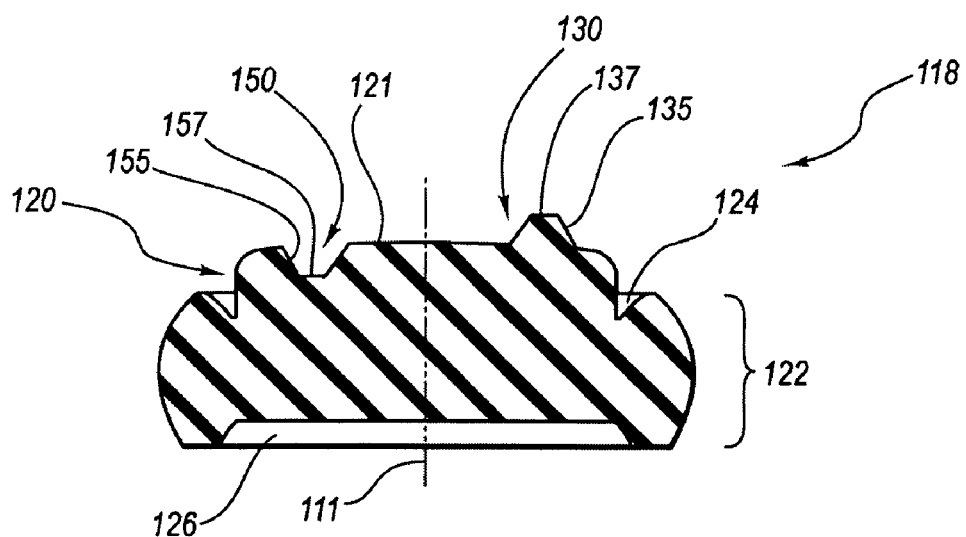

In other embodiment contemplated by the instant disclosure, a septum may include at least one protrusion and at least one recess configured for perception and identification of the septum. For example, FIGS. 27 and 28 show a perspective view and a schematic side cross-sectional view (taken through recess 150 and protrusion 130), respectively, of a septum 118 including a recess 140 and a protrusion 130. Recess 140 and protrusion 130 may be structured relative to one another for perception (e.g., visually or by palpation) and identification of the septum 118. As mentioned above, a recess, a protrusion, or both (if present) may be tapered. As shown in FIGS. 27 and 28, each of recess 140 and protrusion 130 taper generally with respect to an increasing distance from septum surface 121. More particularly, as shown in FIG. 28, recess 140 is defined by a tapered side surface 145 and a substantially planar surface 147. As shown in FIG. 28, tapered side surface 145 is frustoconical and increases in size with respect to an increase in distance from septum surface 121. In addition, as shown in FIG. 28, protrusion 130 is defined by a tapered side surface 135 and a substantially planar surface 137. As shown in FIG. 28, tapered sidewall 135 is frustoconical and decreases in size with respect to an increasing distance from septum surface 121. Of course, either of recess 140 or protrusion 130 may increase in size with respect to an increasing distance from septum surface 121, if desired. Furthermore, as mentioned above, a cross-sectional shape of either of recess 140 or protrusion 130 may be selected from any number of geometries as known in the art. Accordingly, a tapered side surface forming a tapered recess or protrusion may define a frustum exhibiting a selected geometry. In summary, the combination of at least one recess and at least one protrusion may comprise at least one identifiable feature of a septum and may be beneficial for perception and identification of such a septum.

Figure 29:
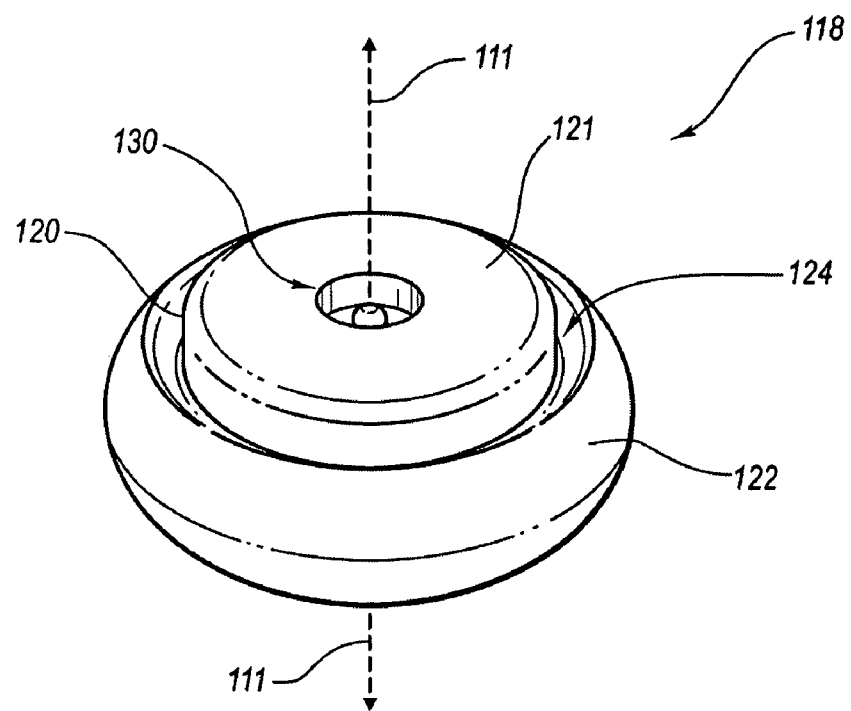
FIGS. 29 and 30 show a perspective view and a schematic side cross-sectional view, respectively, of a septum including a recess and a protrusion, wherein the protrusion is positioned generally within the recess.
Figure 30:
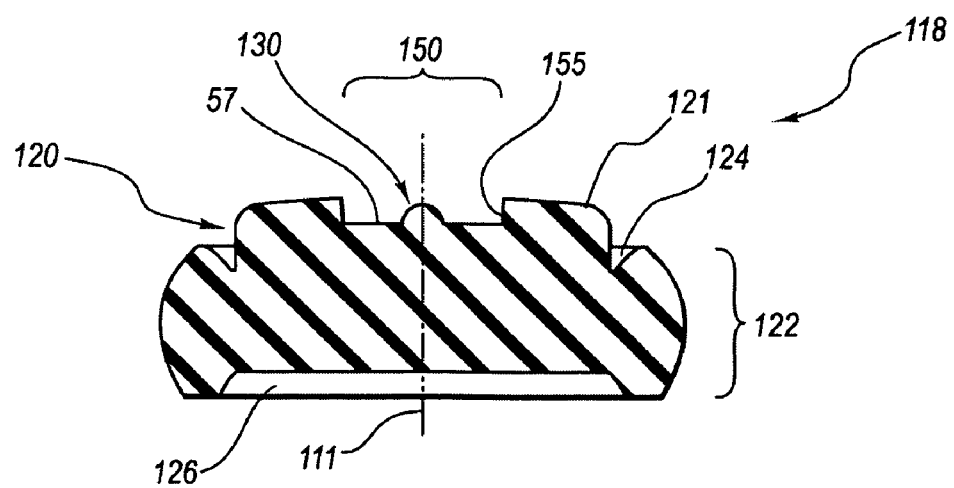

The instant disclosure contemplates various configurations of a septum including at least one protrusion and at least one recess. For example, FIGS. 29 and 30 show a perspective view and a schematic side cross-sectional view, respectively, of a septum 118 including a recess 150 and a protrusion 130. Further, as shown in FIGS. 29 and 30, protrusion 130 is positioned generally within recess 150. Also as shown in FIGS. 29 and 30, both recess 150 and protrusion 130 may be generally centered with respect to central access 111. Of course, in other embodiments, neither of recess 150 nor protrusion 130 may be centered with respect to central access 111. In addition, protrusion 130 may be positioned upon and may extend from any portion of substantially planar surface 157 or sidewall surface 155, without limitation.

Figure 31:
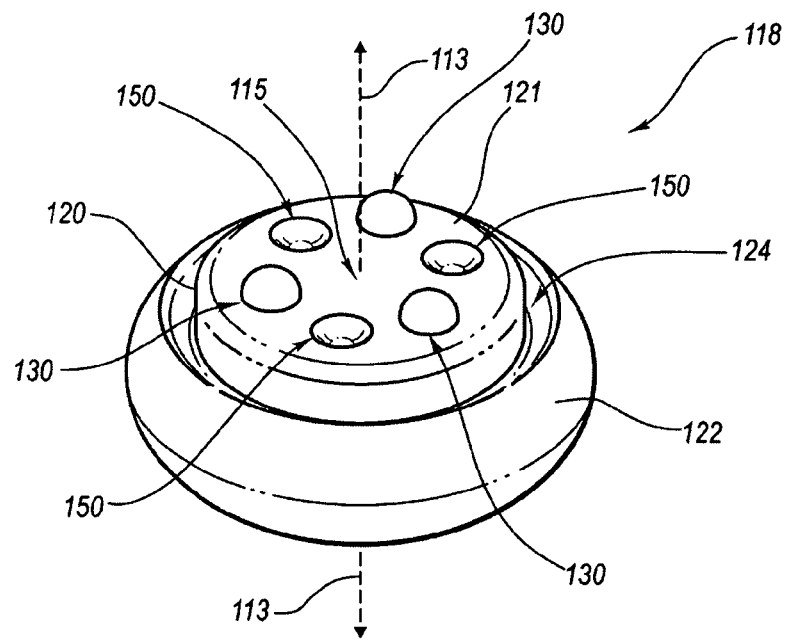
FIG. 31 shows a perspective view of a septum including a plurality of protrusions and a plurality of recesses positioned about a center of revolution.

Accordingly, the instant disclosure contemplates that at least one protrusion, protruding region, recess, recessed region, undulation, or adjacent features of different elevation may comprise a feature for identifying a septum of an access port. For example, in a further embodiment, a plurality of protrusions 80 may be spaced about a selected center or other point on a septum surface of a septum. FIG. 31 shows a perspective view of an exemplary embodiment of a septum 118 including protrusions 130 positioned substantially symmetrically about a center of revolution 115. Center of revolution 115, as shown in FIG. 31, is a point upon septum surface 121 with which axis 113 intersects. Axis 113 may be aligned with a central axis of septum 118, or may be otherwise positioned or oriented. Thus, protrusions 130 may be substantially equidistantly spaced from center of revolution 115 and may be substantially equally circumferentially spaced with respect to one another and about center of revolution 115. Similarly, a plurality of recesses 150 may be substantially symmetrically spaced about center of revolution 115. In another embodiment, one or more of protrusions 130, one or more recesses 150, or both may be positioned upon one or more selected closed plane figure (e.g., a circle, ellipse, rectangle, triangle, etc.) for identifying a septum.

Figure 32:
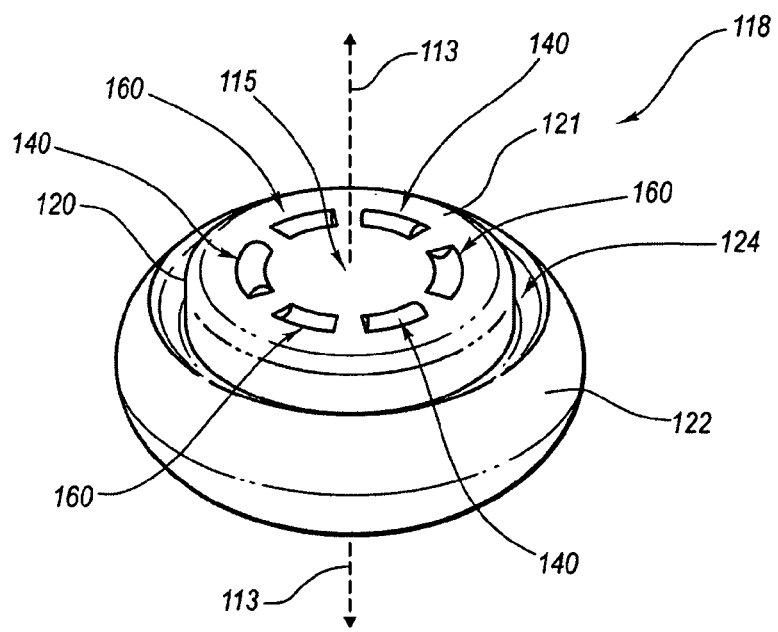
FIG. 32 shows a perspective view of a septum including a plurality of elongated protrusions and a plurality of elongated recesses.

Further, in another embodiment, a topography of a septum may comprise elongated protrusions and elongated recesses. FIG. 32 shows a perspective view of one embodiment of such a septum, including alternating, circumferentially extending, elongated protrusions 140 and circumferentially extending, elongated recesses 160. Optionally, the circumferentially extending, elongated protrusions 140 may be circumferentially substantially equal in size with respect to the circumferentially extending, elongated recesses 160. In another embodiment a septum may exhibit an upper topography comprising alternating, circumferentially extending, elongated protrusions and circumferentially extending, elongated recesses that are unequal in circumferential size. Optionally, it may be appreciated that, optionally, transition regions may extend circumferentially between circumferentially extending, elongated protrusions 140 and circumferentially extending, elongated recesses 160. Such transition regions may taper or generally smoothly transition between a circumferentially extending, elongated protrusion 140 (or any other protrusion or protruding region) and an adjacent circumferentially extending, elongated recess 160 (or any other recess or recessed region). Thus, such transition regions may form an undulating topography that generally smoothly transitions between circumferentially adjacent protrusions and recessed regions.

It should also be understood that the instant disclosure contemplates access ports having a septum with an exposed surface defined, at least in part, by a periphery that is not circular in nature. Rather, the instant disclosure contemplates that an access port may have a periphery which is generally quadrilateral, generally rectangular, generally triangular, generally elliptical, generally oval, generally polygonal, or otherwise configured. It should also be understood from the discussion of the above-described various embodiments of a septum of an access port that variations, additions, combinations, or different features are encompassed by the instant disclosure. Thus, the instant disclosure is not limited to the above-described exemplary embodiments.

Generally, the instant disclosure contemplates that means for identifying a septum may be provided. In one embodiment, as described above, at least one topographical feature may comprise means for identifying a septum. In another embodiment, at least one visual feature may be perceived and used to identify a septum. For example, a color, a pattern, one or more letters, one or more numbers, symbols, any indicia, or combinations thereof, may be formed upon or as a portion of a septum. Such a configuration may allow for visual perception and identification of a septum. In addition, the instant disclosure also contemplates that at least one feature of an access port of the instant disclosure may not be observable visually or by palpation but, rather, may be otherwise observable. For example, means for identifying a septum may comprise at least one feature observable through interaction with an imaging technology such as x-ray or ultrasound. For instance, a metal feature (e.g., a plate or other metal geometry) may be included within a septum of an access port. As may be appreciated, such a metal feature may be represented on an x-ray generated by exposure of the access port to x-ray energy while simultaneously exposing x-ray sensitive film to x-ray energy passing through the access port. Further, the instant disclosure contemplates that a size, shape, or both size and shape of a metal feature of an access port may be configured for enhancing identification of an access port. For example, assuming that a metal feature comprises a metal plate, a size, shape, or both may be selectively tailored for identification of a septum. Similarly, a feature of an access port of the may be tailored for detection via ultrasound interaction. Such a feature may comprise an exterior topographical feature. In another embodiment, such a feature may comprise a composite structure including two or more materials that form an interface (i.e., an interior feature or surface) that may be identified by ultrasound imaging. In a further aspect of the instant disclosure, it is contemplated that a communicative technology may be utilized wherein information is encompassed by an access port of the instant disclosure. Generally, a communication device (e.g., a radio beacon, a light-emitting element, an ultrasound emitting transducer, etc.) may be imbedded or otherwise affixed to a septum of the instant disclosure. Such a communication device may be configured for transmitting information in response to a given impetus. More specifically, a septum may be exposed to a request signal (e.g., a sound, an impact or an acceleration, light, radio waves, etc.). Such a request signal may cause the communication device to transmit information therefrom via sound, light, radio waves, or as otherwise known in the art. Such information may be employed for identifying an access port of the instant disclosure. Thus, a wide variety of means for identifying a septum may be employed for identifying a septum.

In one exemplary example, radio frequency identification technology may be employed for identification of a septum of an access port. Particularly, so-called active RFID tags are powered by an internal battery and are typically read/write devices. Currently, a suitable cell coupled to suitable low power circuitry can ensure functionality for as long as ten or more years, depending upon the operating temperatures and read/write cycles and usage. So-called passive RFID tags operate without a separate external power source and obtain operating power generated from the reader. Passive RFID tags are typically programmed with a unique set of data (usually 32 to 128 bits) that cannot be modified. Read-only tags may operate as an identifier comparable to barcodes, which may contain selected product-specific information. Thus, passive RFID tags may be much lighter than active RFID tags, less expensive, and may offer a substantially unlimited operational lifetime. In one embodiment, an RFID tag may be affixed to an exterior surface of a septum. In another embodiment, an RFID tag may be imbedded within a septum. One advantage of RFID approach is the noncontact, non-line-of-sight nature of the technology. RFID tags can be read through a variety of visually and environmentally challenging conditions, where other optically related technologies may be less effective.

Figure 33:
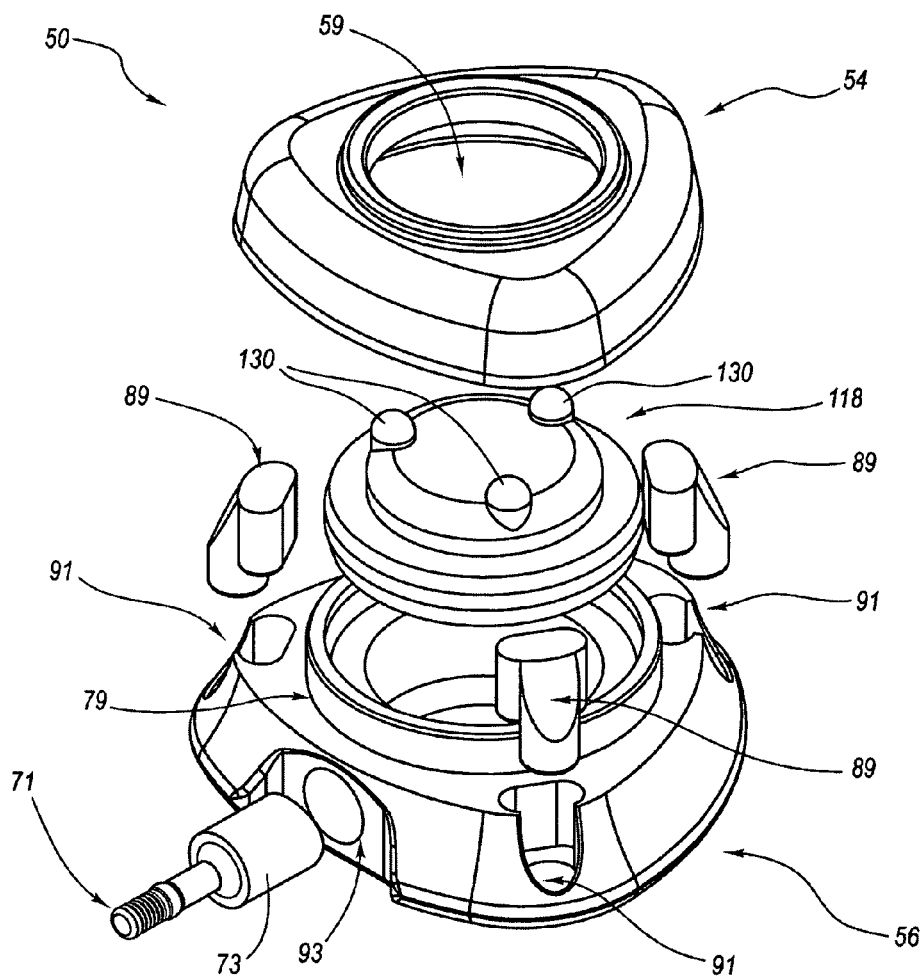
FIG. 33 shows an exploded assembly view of one embodiment of an access port according to the instant disclosure.

As will be appreciated by those skilled in the art, any septum configured according to the above described aspects of the instant disclosure may be incorporated within a housing or body to form an access port. For example, FIG. 33 shows an exploded assembly view of one embodiment of an access port 50 including a septum 118 that comprises a plurality of protrusions 130. More particularly, septum 118 may be positioned between a cap 54 and base 56 (collectively forming a housing) to form an access port 50. As shown in FIG. 33, base 56 may include a raised retaining wall 79 forming a recess into which septum 118 may be positioned. Further, cap 54 may fit generally about the raised retaining wall 79 and may capture septum 118 between base 56 and septum 54 to form a cavity within the access port 50. Also, aperture 59 may be formed by cap 54 and may allow access to septum 118 when the septum 118 is captured between cap 54 and base 56. Further, as shown in FIG. 33, outlet stem 71 may include a stem base 73 that may be positioned within and sealed to an outlet recess 93 formed within base 56. Of course, the outlet stem 71 may be in fluid communication with a cavity formed within the access port 50. Optionally, suture plugs 89 may be positioned within suture cavities 91 formed in base 56. Suture plugs 89 may comprise a pliant material (e.g., silicone, rubber, etc.) that may provide some resilience between sutures coupling the access port (i.e., the base 56) to a patient.

Figure 34:
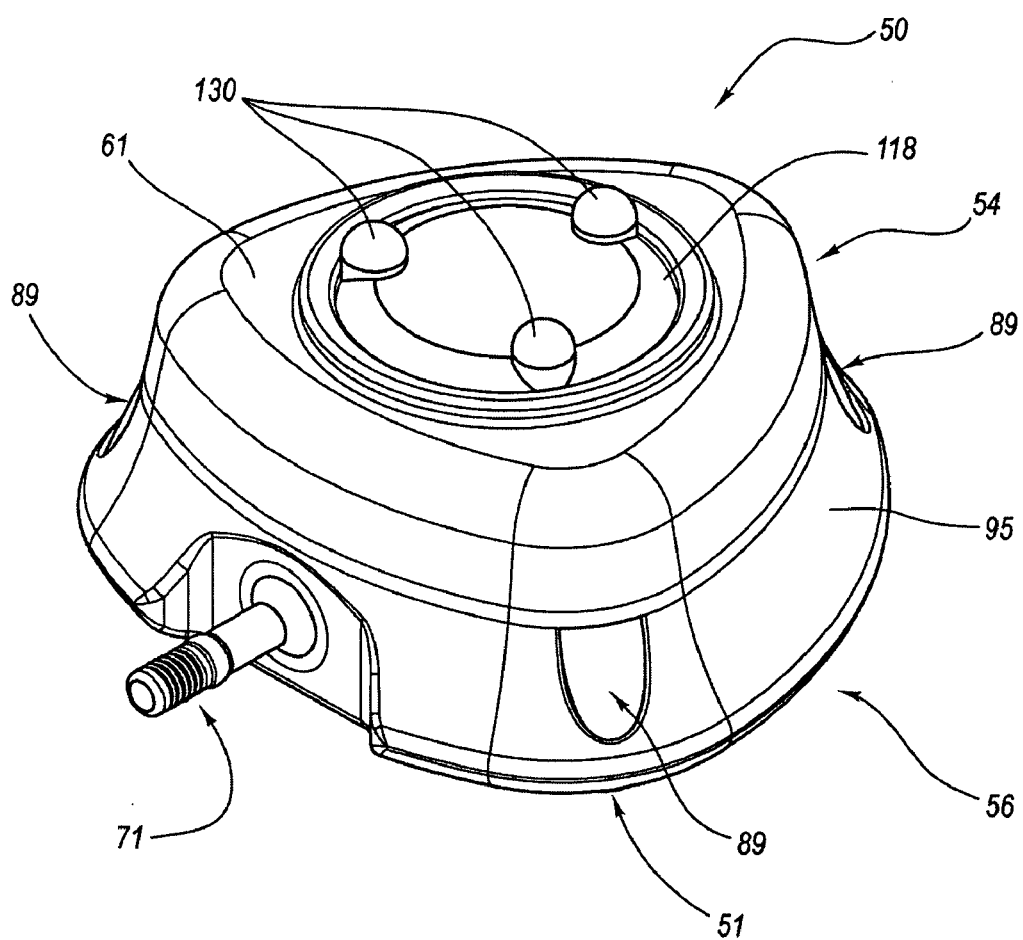
FIG. 34 shows a perspective view of the assembled access port shown in FIG. 33.
Figure 35:
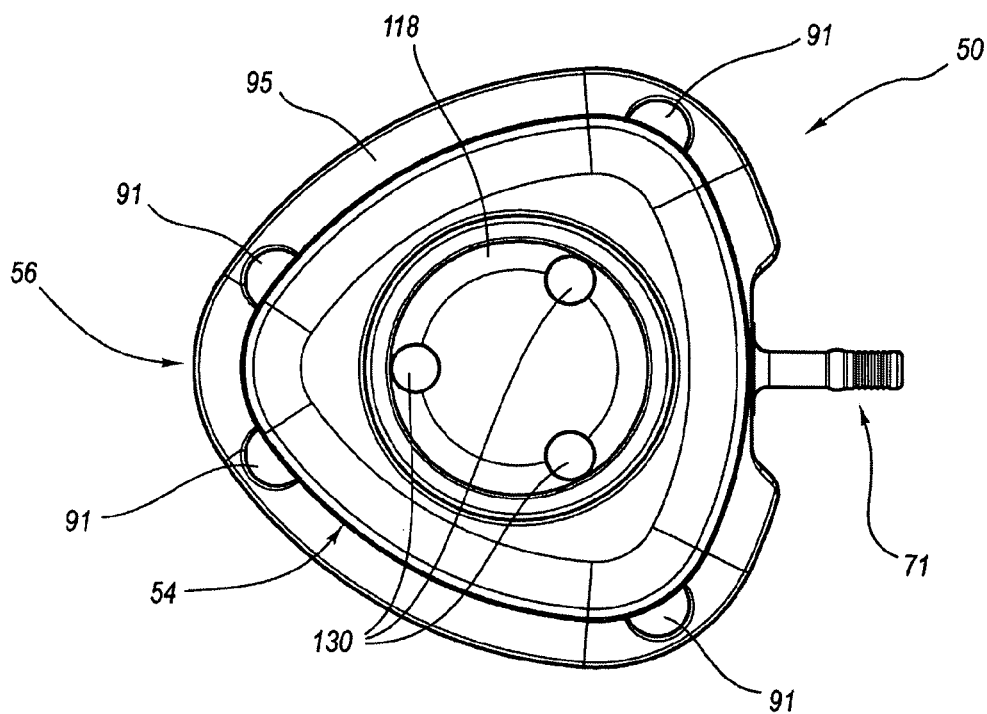
FIG. 35 shows a top elevation view of the assembled access port shown in FIG. 34.
Figure 36:
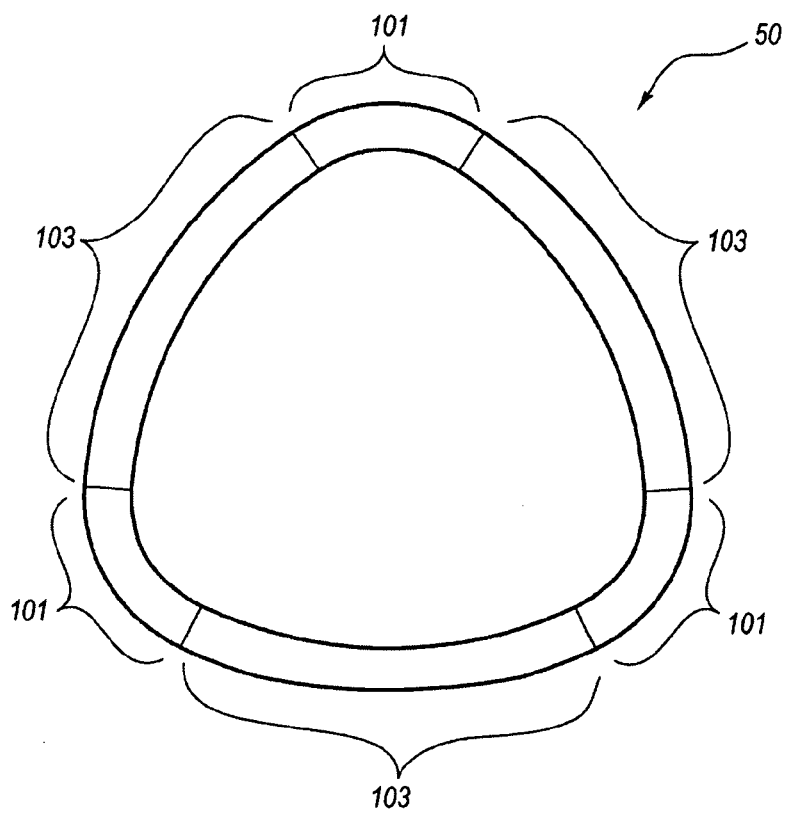
FIG. 36 shows a simplified representation of a transverse cross section of the access port shown in FIGS. 33-35.

In further detail, FIG. 34 shows a perspective view of an assembled access port 50. As shown in FIG. 34, a side periphery 95 (e.g., one or more side walls) of access port 50 may be generally triangular. Thus, cap 54 and base 56 may collectively form a generally triangular housing or body of access port 50. Also, the instant disclosure contemplates that side periphery 95 may taper or arcuately extend between upper surface 61 of cap 54 and lower surface 51 of base 56. As shown in FIG. 34, a transverse cross section (taken in a selected plane substantially parallel to lower surface 51, if planar, of base 56) of access port 50 may be larger proximate to lower surface 51 of base 56 and may be relatively smaller proximate upper surface 61 of cap 54. FIG. 35 shows a top elevation view of the access port 50 shown in FIG. 35 and illustrates a generally triangular shape defined by side periphery 95. Additionally, FIG. 36 shows a simplified representation of a transverse cross section of access port 50. As shown in FIG. 36, side periphery 95 of access port 50 may define three side regions 103 that extend between associated vertex regions 101. In addition, in one embodiment and as shown in FIG. 36, side periphery 95 may define a substantially equilateral generally triangular shape. As may be appreciated, side regions 103 may arcuately extend between associated vertex regions 101; thus, side regions 103 may form "sides" of a generally triangular shape. Further, although vertex regions 101 are rounded, it may be appreciated that such vertex regions 101 form an intersection between adjacent side regions 103. Accordingly, it may be appreciated that the phrase "generally triangular," as used herein, encompasses any generally three-sided geometry wherein adjacent sides intersect, without limitation. For example, "generally triangular" encompasses three sided polygons, circular triangles, equilateral triangles, etc., without limitation.

While certain representative embodiments and details have been shown for purposes of illustrating aspects of the instant disclosure, it will be apparent to those skilled in the art that various changes in the methods and apparatus disclosed herein may be made without departing from the scope of the instant disclosure, which is defined in the appended claims. For example, other access port sizes and shapes may be employed; and various other embodiments and structures may be employed for forming at least one identifiable feature of an access port of the instant disclosure.

What is claimed is:

1. An access port for providing subcutaneous access to a patient, comprising:
    a body capturing a septum that covers a cavity defined by the body; and
    a pattern of protrusions extending from an outer surface of the septum away from the cavity, the pattern of protrusions detectable through palpation to identify the access port as a power-injectable port.

2. The access port according to claim 1, wherein the pattern of protrusions comprises three substantially identical protrusions.

3. The access port according to claim 2, wherein the three substantially identical protrusions are positioned substantially equidistantly from a central axis of the septum in a triangular pattern.

4. The access port according to claim 1, wherein the pattern of protrusions comprises protrusions that are elongated and extend linearly or arcuately.

5. The access port according to claim 4, wherein the elongated protrusions form a plurality of substantially linear ridges.

6. The access port according to claim 5, wherein the substantially linear ridges are parallel to each other.

7. The access port according to claim 6, wherein the parallel substantially linear ridges are formed equidistant from a central axis.

8. The access port according to claim 4, wherein the elongated protrusions intersect substantially near the center of the septum and extend at least partially toward a periphery thereof.

9. The access port according to claim 8, wherein the elongated protrusions extend to the periphery of the septum.

10. The access port according to claim 4, wherein the elongated protrusions form a pattern of intersecting lines.

11. The access port according to claim 1, wherein the protrusions comprise frustoconical circumferential sides and a flat top surface.

12. The access port according to claim 1, further comprising at least one recess extending into the outer surface of the septum.

13. The access port according to claim 12, further comprising three recesses extending into the outer surface of the septum positioned substantially equidistant from the central axis of the septum.

14. The access port according to claim 1, further comprising a plurality of recesses on the outer surface of the septum extending into the septum.

15. The access port according to claim 14, wherein the plurality of recesses and the pattern of projections are positioned equidistant from an axis of the access port, such that an elongated recess is separated from an adjacent elongated recess by a projection.

16. The access port according to claim 15, wherein the recesses and the projections are curved to create a generally circular pattern.

17. The access port according to claim 1, wherein each of the protrusions includes a surface remote from the outer surface of the septum that is rounded.

18. The access port according to claim 1, wherein a side periphery of the access port is generally triangular.

19. A method of identifying a subcutaneously implanted access port, comprising:
    providing an access port including a septum having a pattern of protrusions extending from an outer surface thereof, the pattern of protrusions detectable through palpation to identify the access port as a power-injectable port;
    detecting the protrusions through palpation; and
    identifying the access port as a power-injectable port.

* * * * *